US008969241B2

(12) United States Patent
Ha et al.

(10) Patent No.: US 8,969,241 B2
(45) Date of Patent: Mar. 3, 2015

(54) ORGANIC-INORGANIC HYBRID MESOPOROUS SILICA MATERIAL MODIFIED BY SULFONIC ACID GROUP FOR SELECTIVE ADSORPTION OF METAL IONS AND METHOD OF MANUFACTURING THE SAME

(75) Inventors: Chang-Sik Ha, Pusan (KR); Sang Hyun Lee, Pusan (KR); Sung Soo Park, Pusan (KR)

(73) Assignee: Pusan National University Industry—University Cooperation Foundation (KR)

( * ) Notice: Subject to any disclaimer, the term of this patent is extended or adjusted under 35 U.S.C. 154(b) by 253 days.

(21) Appl. No.: 13/603,923

(22) Filed: Sep. 5, 2012

(65) Prior Publication Data
US 2013/0303766 A1    Nov. 14, 2013

(30) Foreign Application Priority Data
May 9, 2012    (KR) .................. 10-2012-0049628

(51) Int. Cl.
*B01J 20/00* (2006.01)
*B01J 20/02* (2006.01)
*B01J 20/10* (2006.01)
*B01J 20/28* (2006.01)
*C07F 7/02* (2006.01)

(52) U.S. Cl.
USPC ............................ 502/407; 502/408; 546/14

(58) Field of Classification Search
CPC ............. C07F 7/02; B01J 20/00; B01J 20/02; B01J 20/0251; B01J 20/10; B01J 20/28
See application file for complete search history.

(56) References Cited

PUBLICATIONS

Liu et al. "Luminescent film with terbium-complex-bridged polysilsesquioxanes", New Journal of Chemistry, 2003, 27, 233-235.*

* cited by examiner

*Primary Examiner* — Robert S Loewe
(74) *Attorney, Agent, or Firm* — Park & Associates IP Law, P.C.

(57) ABSTRACT

A silica precursor having a selective adsorptivity with respect to cobalt ions is disclosed. The silica precursor includes a cross-linked 2,6-diamino pyridine group obtained by using 2,6-diamino pyridine, phosgene and 3-aminopropyltriethoxysilane.

10 Claims, 24 Drawing Sheets

| SAMPLE | BET surface area (m²/g) | Pore volume (cm²/g) | Pore size (Å) |
|---|---|---|---|
| 3% DAP-PMO | 637 | 0.69 | 43 |
| 6% DAP-PMO | 432 | 0.53 | 49 |
| 12% DAP-PMO | 196 | 0.23 | 48 |
| 18% DAP-PMO | 38 | 0.05 | 52 |
| 24% DAP-PMO | 12 | 0.02 | 58 |

FIG. 17
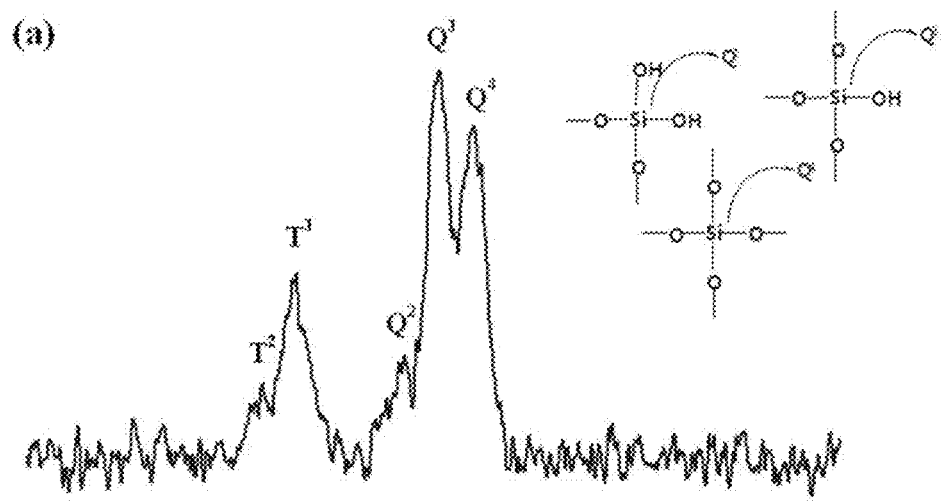
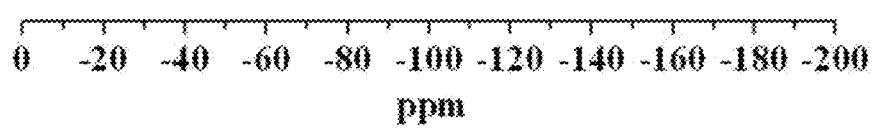
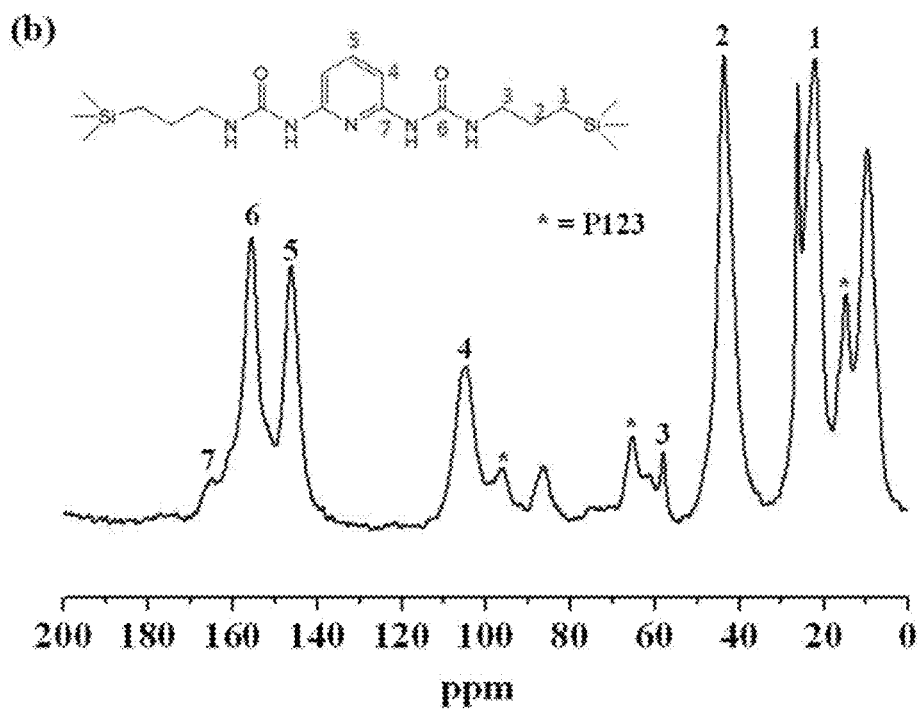

| SAMPLE | BET surface area (m²/g) | Pore volume (cm²/g) | Pore size (Å) |
|---|---|---|---|
| 3% SAM-PMO | 348 | 0.43 | 49 |
| 6% SAM-PMO | 292 | 0.39 | 51 |
| 12% SAM-PMO | 64 | 0.1 | 53 |
| 18% SAM-PMO | 18 | 0.02 | 54 |

FIG. 25

| METAL ION SPECIES | Co²⁺ | | Cr³⁺ | | Ni²⁺ | | Cu²⁺ | | Li⁺ | |
|---|---|---|---|---|---|---|---|---|---|---|
| SAMPLE | ADSORPTION AMOUNT (mg/g) | SELECTIVITY (%) | ADSORPTION AMOUNT (mg/g) | SELECTIVITY (%) | ADSORPTION AMOUNT (mg/g) | SELECTIVITY (%) | ADSORPTION AMOUNT (mg/g) | SELECTIVITY (%) | ADSORPTION AMOUNT (mg/g) | SELECTIVITY (%) |
| 3% SAM-PMO | 2.54 | 86 | 0 | 0 | 0.12 | 12 | 0 | 0 | 0.19 | 19 |
| 6% SAM-PMO | 4.49 | 96 | 0 | 0 | 0 | 0 | 0.0025 | 0.053 | 0.18 | 3.9 |
| 12% SAM-PMO | 4.86 | 74 | 0 | 0 | 0.93 | 14 | 0.62 | 9.3 | 0.19 | 2.9 |
| 18% SAM-PMO | 2.8 | 52 | 0.06 | 1.2 | 0.13 | 2.4 | 0.98 | 18 | 0.18 | 3.4 |

COMPONENT OF ARTIFICIAL SEAWATER: (24.3g NaCl, 5.14g MgCl₂, 1.14g CaCl₂, 0.69g KCl, 0.2g NaHCO₃, 0.1g KBr, 0.027g H₃BO₃, 0.026g SrCl₂, 0.004g NH₄Cl, 0.003g NaF, 0.002g Na₂SiO₃, 0.001g FePO₄) / L

ORGANIC-INORGANIC HYBRID MESOPOROUS SILICA MATERIAL MODIFIED BY SULFONIC ACID GROUP FOR SELECTIVE ADSORPTION OF METAL IONS AND METHOD OF MANUFACTURING THE SAME

REFERENCE TO RELATED APPLICATIONS

This application claims the priority benefit of Korean Patent Application No. 10-2012-0049628 filed on May 9, 2012, the entire contents of which are incorporated herein by reference.

FIELD OF THE INVENTION

The present invention relates to an organic-inorganic hybrid mesoporous silica material modified by a sulfonic acid group and a method of manufacturing the same, and more particularly, to an organic-inorganic hybrid mesoporous silica material which may selectively adsorb metal ions.

BACKGROUND OF THE INVENTION

Generally, seawater and waste water from a factory include a large amount of heavy metals and organic or inorganic contaminants and so are not good to humans. Recently, various harmful materials are generated in line with the development and the rapid growth of an industrial society and so, problems concerning an environmental contamination become intensified. Accordingly, development on a treating agent of the harmful materials is on demand.

In order to adsorb metal ions from an aqueous solution, a chelate ion-exchange resin, an activated carbon, an acryl amide polymer fiber, etc. may be used (S. Deng, R. Bai, J. P. Chen, *J. Colloid and Interface Sci.* 2003, 260, 265). Among the above described methods, the chelating method is mainly used for an isolation and condensing system. Particularly, chelating ligands illustrate specific adsorptivity onto heavy metals (O. Guvan, P. A. Kavakali, *J. Appl. Polym. Sci.* 2004, 93, 1705).

A method of manufacturing mesoporous materials using silica as a porous wall constituting material and a surfactant as a template material, has been reported by Kresge et al. for the first time (C. T. Kresge, M. E. Leonowitz, W. J. Roth, J. C. Vertuli, J. S. Beck, *Nature,* 1992, 359, 710). The mesoporous materials have a regular and porous structure (a cubic structure, a hexahedral structure, a worm structure), a high surface area (about 1,000 $m^2/g$ or over), and a homogeneous pore size, and so have a diverse application possibility.

Organic-inorganic hybrid mesoporous materials including inorganic silica as a porous wall along with a cross-linked organic material (trialkoxy silane including a cross-linked bonding of methane, ethane, butane, ethylene, acetylene, thiophene, bithiophene, phenyl, biphenyl and derivatives thereof) have been prepared {(a) Landskron, K.; Hatton, B. D.; Perovic D. D.; Ozin, G. A. *Science* 2003, 302, 266 (b) kapoor, M. P.; Inagaki, S. Bull. *Chem. Soc. Jpn.* 2006, 79, 1463 (c) Lu, Y.; Fan, H.; Doke, N.; Loy, D. A.; Assink, R. A.; LaVan, D. A.; Brinker, C. J. *J. Am. Chem. Soc.* 2000, 122, 5258 (d) C. Vercaemst, P. E. de Jongh, J. D. Meeldijk, B. Goderis, F. Verpoort, P. Van Der Voort, *Chem. Commun.,* 2009, 4052}.

The organic-inorganic hybrid mesoporous materials have a high surface area (about 700 $m^2/g$ or over), a homogeneous pore size (about 250 nm), a regular porous structure (a cubic structure, a hexahedral structure, a worm structure), good physical properties, an advantageous modification property of the surface portion of the pores, a high adsorptivity and a chemical stability. Accordingly, the organic-inorganic hybrid mesoporous materials have a high application possibility including adsorption of macromolecules, adsorption of enzymes, adsorption of metal ions, a catalyst reaction, a sensor, a drug delivery, a preparation of nano material, etc. {(a) F. Hoffmann, M. Cornelius, J. Morell, M. Froba, *Angew. Chem. Intl. Ed.,* 2006, 45, 3216 (b) K. H. Hossain, L. Mercier, *Adv. Mater.,* 2002, 14, 1053 (c) Fukuoka, A.; Sakamoto, Y.; Guan, S.; Inagaki, S.; Sugimoto, N.; Fukushima, Y.; Hirahara, K.; lijima, S.; Ichikawa, M. *J. Am. Chem. Soc.* 2001, 123, 3373 (d) Burleigh, M. C.; Dai, S.; Hagaman, E. W.; Lin, J. S. *Chem. Mater.* 2001, 13, 2537; Yang, Q.; Kapoor, M. P.; Inagaki, S. *J. Am. Chem. Soc.* 2002, 124, 9694 (e) Yamamoto, K.; Nohara, Y.; Tatsumi, T. *Chem. Lett.* 2001, 648 (f) kapoor, M. P.; Bhaumik, A.; Inagaki, S.; Kuraoka, K.; Yazawa, T. *J. Mater. Chem.* 2002, 12, 3078 (g) Bhaumik, A.; Kapoo, M. P.; Inagaki, S. *Chem. Commun.* 2003, 470 (h) Ying, J. Y. C.; Mehnert, P.; Wong, M. S. *Angew. Chem., Int. Ed.* 1999, 38, 56 (i) Davis, M. E. *Nature* 2002, 417, 813}. Recently, the organic-inorganic hybrid mesoporous materials are known to have a high application possibility in adsorbing heavy metals from waste water {(a) C. Z. Huang, B. Hu, Z. C. Jiang, *Spectrochim. Acta* part B 2007, 62, 454 (b) S. R. Yousefi, M. Salavati-Niasari, *Talanta* 2009, 80, 212}.

The manufacture of the mesoporous materials including various cross-linked organic materials in the porous wall has a limitation. Generally, the mesoporous materials including the various cross-linked organic materials may be manufactured by simultaneously mixing a surfactant as a main template material and an organic-inorganic hybrid material as a porous wall forming material. In this case, though the manufacturing process may be simple, cross-linked functional organic groups may be included in the porous wall and so, the porous structure may frequently collapse. In addition, the preparation of a precursor including the various cross-linked functional groups is a difficult task. Therefore, the manufacture of the organic-inorganic hybrid mesoporous materials including various functional groups in the porous wall is difficult {(a) K. H. Hossain, L. Mercier, *Adv. Mater.,* 2002, 14, 1053 (b) M. Kuruk, M Jaroniec, S. Guan, S. Inagaki, *J. Phys. Chem. B,* 2001, 105, 681 (c) M. Alvaro, B. Ferrer, V. Fornes, H. Garcia, *Chem. Commun.,* 2001, 24, 2546 (d) G. Zhu, D. J. Jones, J. Zajac, R. Dutartre, M. Rhomari, J. Rozie, *Chem. Mater.,* 2002, 14, 4886 (e) J. Liu, J. Yang, Q. Yang, G. Wang, Y. Li, *Adv. Puna Mater.,* 2005, 15}.

In order to improve the above-described defect, a post-synthesis method may be applied (F. Hoffmann, M. Cornelius, J. Morell, M. Frba, *Angew. Chem. Int. Ed.* 2006, 45, 321). According to the method, a surfactant or a block copolymer polymer may be used as the template material and an inorganic material such as silica may be used as the porous wall forming material. Through a hydrothermal reaction under an acidic or alkaline condition, an inorganic mesoporous material may be obtained in the first step. In the second step, a reaction of a precursor including an organic group having a functionality is carried out with the surface portion of the pores to fix thereon the organic group having diverse applicability. Silanol (Si—OH) groups present at the surface portion of the pores in the organic-inorganic hybrid mesoporous silica material may be advantageously used for modifying the organic groups having various functional groups. Accordingly, the surface the pores of the mesoporous silica material may be modified using the organic groups having various functional groups and may be expected to have a selective adsorption with respect to metal ions {(a) Q. Cai, W. Y. Lin, F.

S. Xiao, W. Q. Pang, X. H. Chen, B. S. Zuo, *Micropor. Mesopor. Mater,* 1999, 32, 1 (b) B. J. S. Johnson, A. Stein, *Inorg. Chem.* 2001, 40, 801 (c) M. R. Ganjali, A. Daftari, L. Hagiagha-Babaci, *Water, Air, Soil Pollut,* 2006, 173, 71}.

Considering the above, the inventors of the present application has been suggested a silica precursor including a functional group having a cross-linked 2,6-diamino pyridine group.

FIG. 26 illustrates a chemical scheme reported by the present inventors in a society of The 3$^{rd}$ Asian Symposium on Advanced Materials' (Sep. 19, 2011~Sep. 22, 2011).

The silica precursor including a functional group having a cross-linked 2,6-diamino pyridine group may be used as an organic-inorganic hybrid porous wall forming material, and a block copolymer may be used as a template material. Through a hydrothermal reaction, an organic-inorganic hybrid mesoporous silica material may be synthesized and through a post synthesis method using chlorosulfonic acid, an organic-inorganic hybrid mesoporous silica material including a sulfonic acid group in the porous wall may be formed.

However, referring to FIG. 26, in order to obtain the organic-inorganic silica precursor using 2,6-diamino pyridine and 3-isocyanatopropyl triethoxysilane as reacting materials, a refluxing at a temperature of about 85° C. and an atmosphere of an inert gas ($N_2$) may be required to implement a reaction. In addition, the reaction using 3-isocyanato triethoxysilane may require to be performed in a glove box. Further, a side reaction may be readily occurred during performing the synthetic method of the organic-inorganic hybrid silica precursor.

Among ten rare metals (lithium, cobalt, molybdenum, manganese, tungsten, titanium, magnesium, indium, a rare-earth metal, chrome) drawing attention by the government as a part of securing resources, cobalt is mostly coated on an anode of a secondary battery to be used as a main component of an anode material to impart functions of storing and supplying exterior energy. Cobalt is an important rare metal drawing attention as a necessary and strategy metal in the present primary core industry. Considering the circumstances of lacking in the natural resources, the separation and condensation of cobalt as a high value product is very important. Recently, an international price of cobalt is rapidly increasing and a confirmation of the core materials including cobalt is necessary.

The separation and condensation of cobalt has been performed using a metal oxide such as $TiO_2$ as an adsorbing agent {(a) Param H Tewari, Woon Lee, *J Colloid Interface,* 1975, 52, 77 (b) Jae Chun Ryu, Hyun Soo Yang, Yu Hwan Kim, Ki Woung Sung, Yong lk Kim, *J IND ENG CHEM,* 1996, 7, 1192 (c) Hiroki Tamuraa, Noriaki Katayamab, Ryusaburo Furuichia, *J Colloid Interface,* 1997, 195, 192}. However, the structure of the metal oxide may collapse and so the efficiency of the adsorbing agent may decrease (S. J. Hwang, *J. Korean Chem. Soc,* 2004, 48, 46).

Bhattacharyya et al. performed an experiment on cobalt adsorption using an inorganic oxide, montmorillonite (Krishna G. Bhattacharyya, Susmita Sen Gupta, *Applied Clay Science,* 2008, 41, 1-9). However, the adsorption selectivity was not found in a specific artificial solution.

As described above, the metal oxide as the conventional adsorbing agent for performing a selective cobalt adsorption is weak to an environment such as a strong acid, and an inorganic oxide has no adsorption selectivity in a specific artificial solution.

SUMMARY OF THE INVENTION

An object of the present invention is to provide an organic-inorganic hybrid silica precursor having a high surface area, arranged in a high regularity, having a certain size of nanometer degree in a strong acid condition.

Another object of the present invention is to provide an organic-inorganic hybrid mesoporous adsorbing agent having a high selectivity with respect to specific metal ions including cobalt.

According to an aspect of the present invention, there is provided an organic-inorganic hybrid mesoporous silica material modified by a sulfonic acid group and having a very high selectivity with respect to cobalt ions. The mesoporous silica material has a high surface area (about 600 $m^2/g$ or over), has well arranged pores having a homogeneous pore size (about 43.0 Å), has a large pore volume (about 0.69 $cm^3/g$) and has a stable and cross-linked functional group under an acidic condition so that may be possibly synthesized under a strong acid condition.

According to another aspect of the present invention, there is provided a method of manufacturing an organic-inorganic hybrid mesoporous material by means of a sol-gel reaction and a self assembling method using a structure forming template, a structure forming auxiliary agent for regular arrangement of pores, and a pore wall forming material.

Preferably, the pore wall forming material may be a silica source including a cross-linked 2,6-diamino pyridine group.

Preferably, an organic-inorganic hybrid silica source including a functional group may be prepared by using 2,6-diamino pyridine, phosgene and 3-aminopropyltriethoxysilane and may have the following chemical formula.

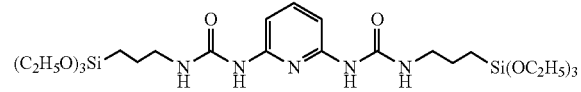

In accordance with exemplary embodiment of the present inventive concept, an organic-inorganic hybrid mesoporous material formed by using a cross-linked 2,6-diamino pyridine group and tetraethyl orthosilicate as a silica source, may be modified using chlorosulfonic acid to modify the pore surface of the organic-inorganic hybrid mesoporous material and to provide an organic-inorganic hybrid adsorbing agent exhibiting a selective adsorptivity with respect to metal ions.

Preferably, a structure forming template may be a surfactant selected from a mono molecule compound such as $CH_3(CH_2)_{11}N(CH_3)_3Br$, $CH_3(CH_2)_{15}N(CH_3)_3Br$, and $CH_3(CH_2)_{17}N(CH_3)_3Br$, a three-element copolymer (poly (ethylene oxide)-block-poly(propylene oxide)-block-poly (ethylene oxide)) of a block copolymer {poly(ethylene oxide) poly(propylene oxide)-poly(ethylene oxide), and a two-element copolymer (poly(ethylene oxide-poly (ethyl ethylene), PEO—PEE)) of the block copolymer.

BRIEF DESCRIPTION OF THE DRAWINGS

The above objects and other advantages of the present invention will become more apparent by describing in detail preferred embodiments thereof with reference to the attached drawings in which:

FIGS. 17A and 17B are NMR spectra of (a) $^{29}$Si and (b) $^{13}$C on an organic-inorganic hybrid mesoporous silica material including a 2,6-diamino pyridine group (12% DAP-PMO).

FIG. 25 is a table for illustrating an adsorbing amount and selectivity with respect to metal ions on a solution including various metal ions dissolved therein and manufactured by using an aqueous solution (artificial seawater) having similar condition as the seawater, as a solvent.

DETAILED DESCRIPTION OF THE INVENTION

Now, preferred embodiments of the present invention will be described in detail with reference to the accompanying drawings. The terms used herein will be defined as follows to help understanding of the present inventive concept.

First, 'template for forming a structure' means 'template used for forming a structure' and 'mesoporous silica material' or 'mesoporous molecular sieve' means porous material having a pore size of about 2~50 nm, and 'functional organic-inorganic hybrid silica source' means an organic-silica compound having an adsorptivity with respect to metal ions.

In accordance with the present inventive concept, the organic-inorganic hybrid mesoporous silica material may be prepared by a simultaneous synthetic process using a three-element copolymer as a template and silica (such as tetraethyl orthosilicate) or an organic-inorganic hybrid silica source (such as an organic-inorganic silica precursor including a 2,6-diamino pyridine group) as a porous wall forming material under an acidic condition.

In addition, an organic-inorganic hybrid adsorbing agent having selective adsorptivity with respect to metal ions may be prepared by modifying and functionalizing an amino group included in a 2,6-diamino pyridine group to a sulfonic acid group by using chlorosulfonic acid.

Figure 1:
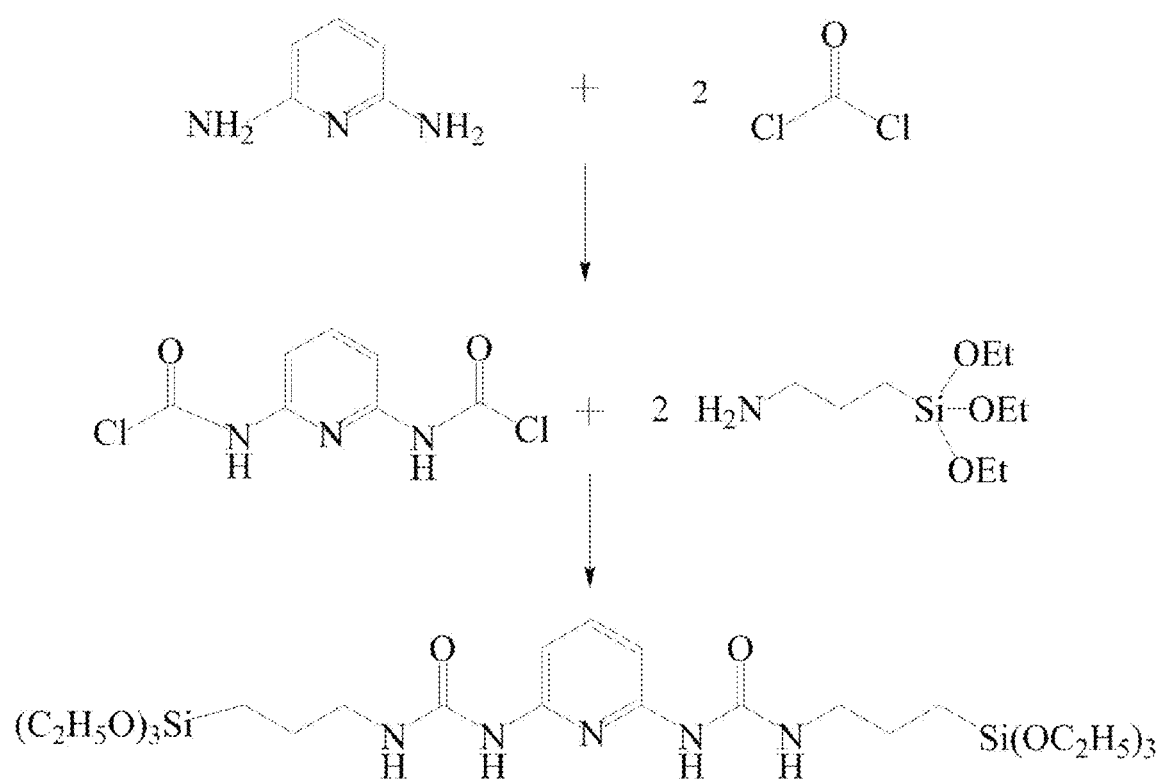
FIG. 1 is a schematic diagram for illustrating a synthetic process of a cross-linked 2,6-diamino pyridine silica precursor.

FIG. 1 is a schematic diagram for illustrating a synthetic process of a cross-linked 2,6-diamino pyridine silica precursor.

An organic-inorganic hybrid silica source including a cross-linked 2,6-diamino pyridine group may be prepared by reacting 2,6-diamino pyridine and phosgene, and 3-aminopropyltriethoxysilane.

Figure 2:
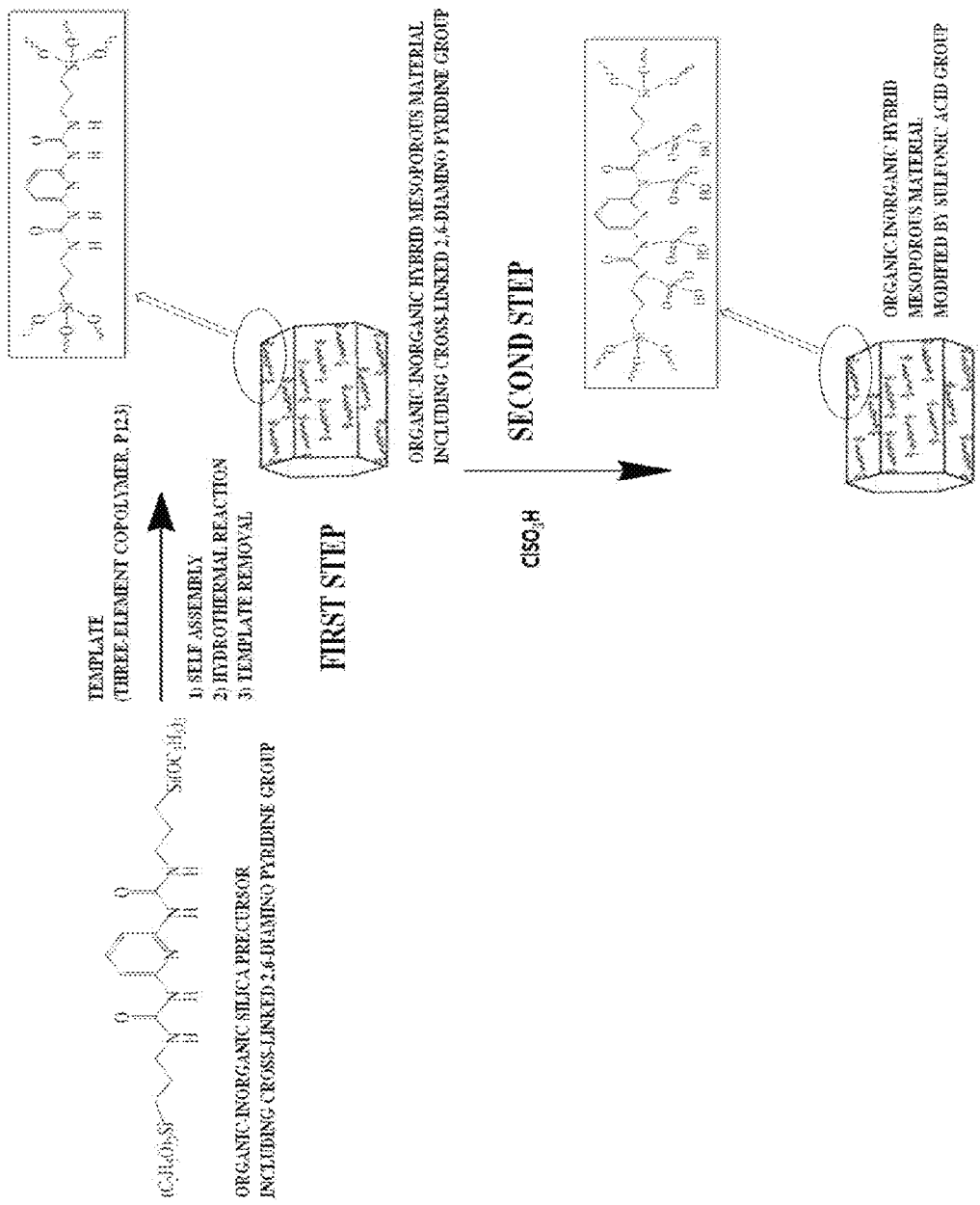
FIG. 2 is a schematic diagram of a preparing process of an organic-inorganic hybrid mesoporous silica material modified by a sulfonic acid group.

FIG. 2 is a schematic diagram of a preparing process of an organic-inorganic hybrid mesoporous silica material modified by a sulfonic acid group, having a large surface area and including regular pores of a nanometer size.

Referring to the first step for preparing the organic-inorganic hybrid mesoporous silica in FIG. 2, a hybrid of silica and template may be obtained by using silica (such as tetraethyl orthosilicate) and a 2,6-diamino pyridine group cross-linked organic-inorganic hybrid silica source as porous wall forming materials and a surfactant or a block copolymer as a template forming material, and by using a sol-gel process and a self-assembly process in the presence of an acid.

Here, the surfactant applicable for forming the template may include $(CH_3(CH_2)_{11}N(CH_3)_3Br$, $CH_3(CH_2)_{15}N(CH_3)_3Br$, $CH_3(CH_2)_{17}N(CH_3)_3Br)$, etc. The block copolymer may include a three-element copolymer {poly(ethylene oxide)-block-poly(propylene oxide)-block-poly (ethylene oxide)} and a two-element copolymer {poly(ethylene oxide)-poly(ethyl ethylene), PEO-PEE} of {poly(ethylene oxide) poly(propylene oxide)-poly(ethylene oxide), etc. More preferably, the block copolymer may include PEO-PPO-PEO block copolymer.

Referring to the second step in FIG. 2, the hybrid of silica and template is aged at about 35° C. and then is made to undergo a hydrothermal reaction at about 80° C.

After obtaining an organic-inorganic mesoporous silica/template material through performing the heating, a drying process at from about 80° C. to about 100° C. is performed. Then, the template is removed using a mixture solution of hydrochloric acid-ethanol to manufacture an organic-inorganic hybrid mesoporous silica material including an organic-inorganic hybrid silica porous wall, having a surface area of about 600 $m^2/g$ or over, and including arranged pores of a nanometer size in regular.

Organic groups introduced into the porous wall may react with an appropriate organic compound to be modified to other functional groups.

Figure 3:
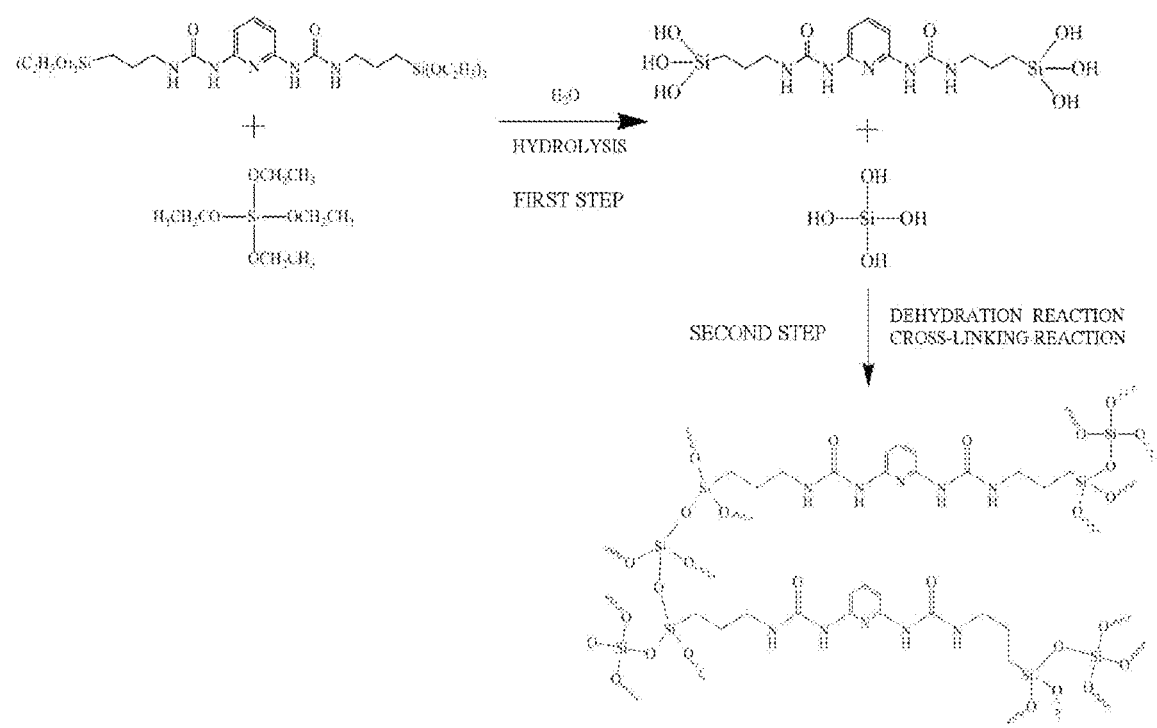
FIG. 3 is a schematic diagram for illustrating a mechanism of forming a porous wall when using tetraethyl orthosilicate and a cross-linked 2,6-diamino pyridine silica precursor as the porous wall forming materials.

FIG. 3 is a schematic diagram for illustrating a mechanism of forming a porous wall when using tetraethyl orthosilicate and a cross-linked 2,6-diamino pyridine silica precursor as porous wall forming materials.

An alkoxy group of a silica source or an organic-inorganic hybrid silica source may be hydrolyzed in an aqueous solution (the first step in FIG. 3). Then, a dehydration reaction may be performed between silanol compounds to form a —Si—O—Si— bond. Cross-linking of —Si—O—Si— bonds may produce the porous wall (the second step in FIG. 3).

Figure 4:
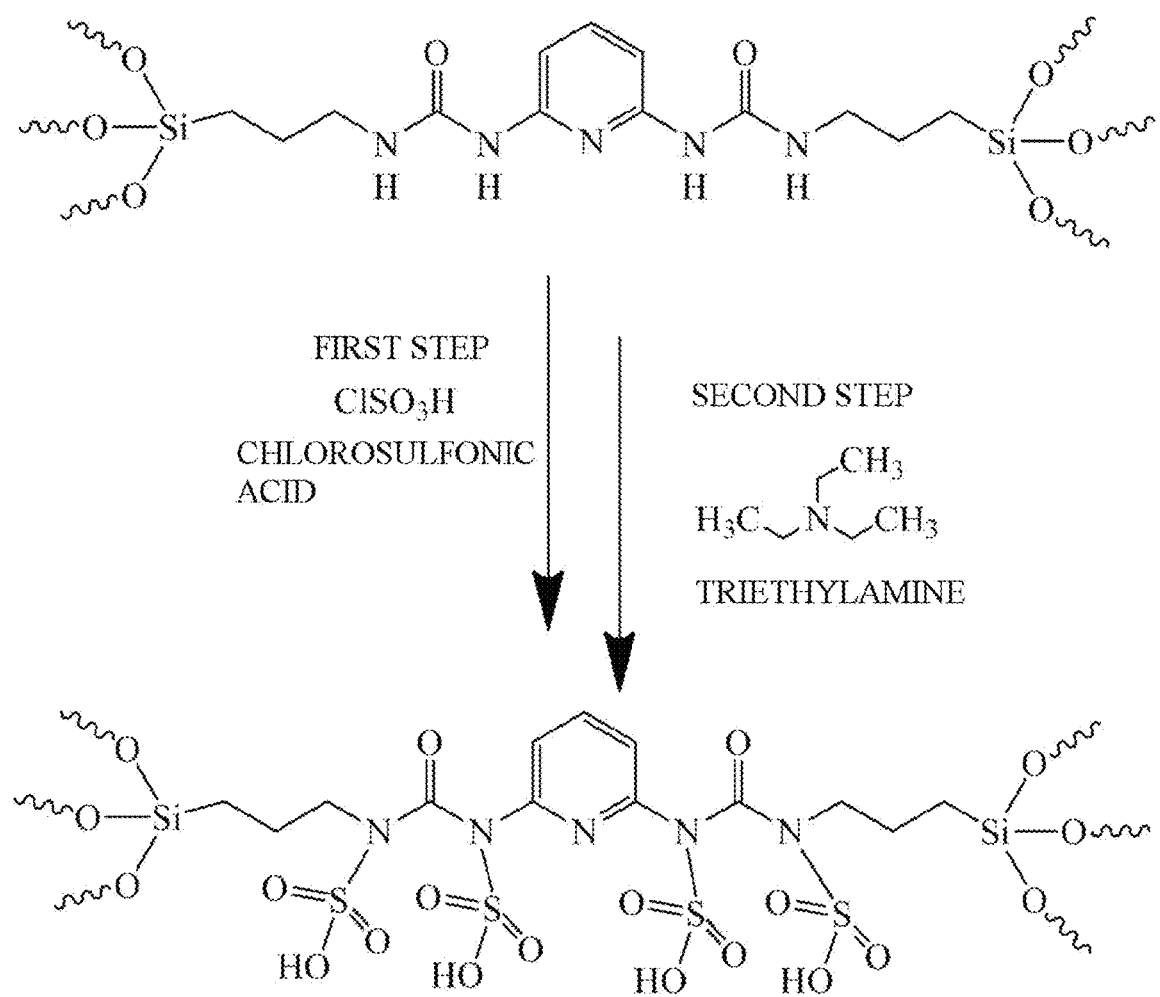
FIG. 4 is a schematic diagram for explaining a modifying process of a nitrile group included in an organic-inorganic hybrid mesoporous silica material having a cross-linked 2,6-diamino pyridine group using a sulfonic acid group.

In addition, organic groups introduced in the porous wall may react with an appropriate organic compound and may be modified to other functional groups. FIG. 4 is a schematic diagram for explaining a modifying process of a nitrile group included in an organic-inorganic hybrid mesoporous silica material including a cross-linked 2,6-diamino pyridine group by using a sulfonic acid group.

Referring to FIG. 4, the amino group is treated in the presence of triethyl amine to be modified to the sulfonic acid group. This process is illustrated only for an exemplary embodiment of the modifying process and so, the modifying process should not be limited to this process.

Figure 5:
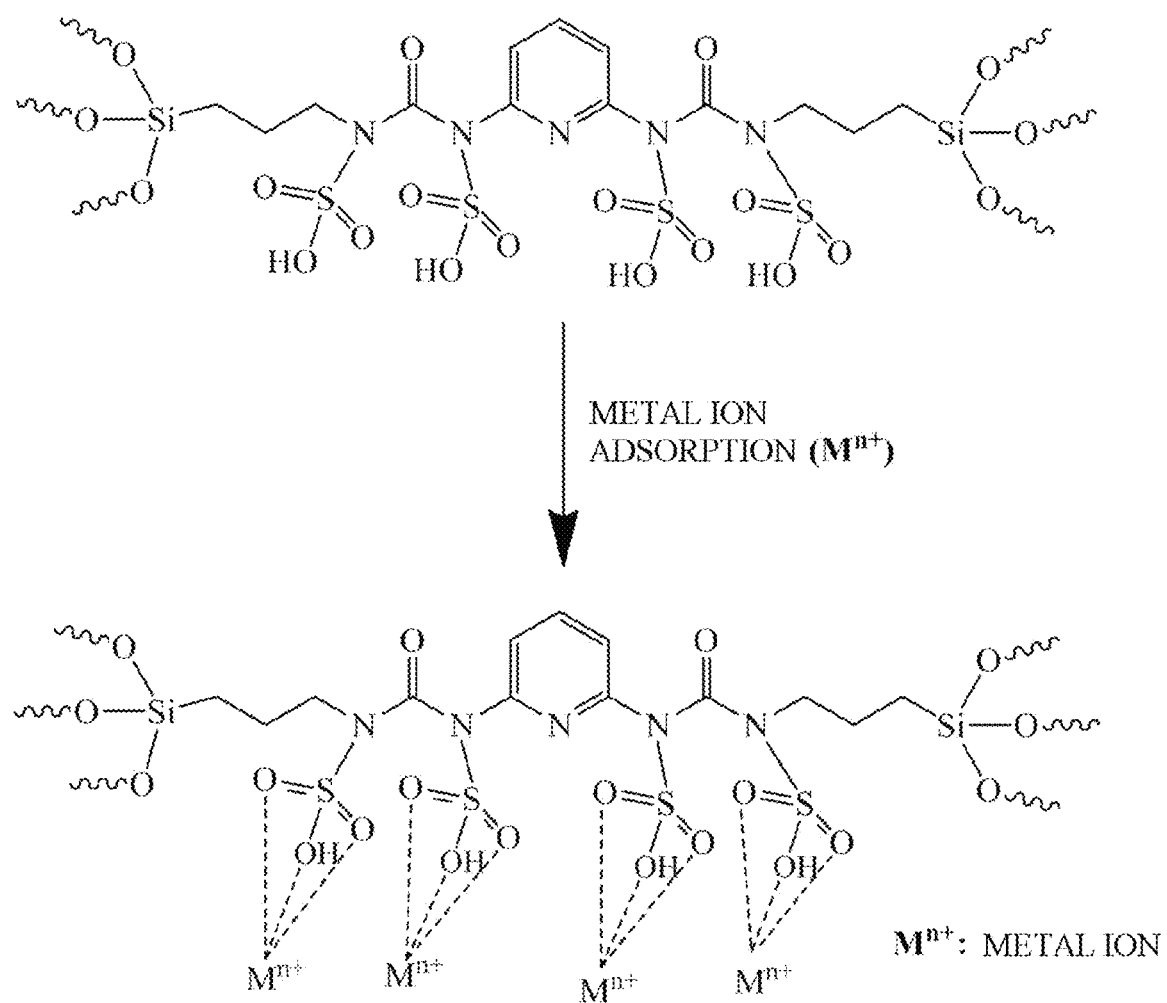
FIG. 5 is a schematic diagram for illustrating an adsorbing process of metal ions using a modified organic-inorganic hybrid mesoporous silica material modified by using a sulfonic acid group.

FIG. 5 is a schematic diagram for illustrating an adsorbing process of metal ions using a modified organic-inorganic hybrid mesoporous silica material by a sulfonic acid group.

Referring to FIG. 5, when an adsorbing agent is added into an aqueous solution of metal ions and then stirred, the metal ions make bonds with the functional groups to be adsorbed.

With respect to the hybrid mesoporous silica material including a sulfonic acid modified organic group as prepared above, the pore size, the particle shape, the constituting material of the porous wall, etc. may be determined through an X-ray diffraction pattern, a nitrogen isothermal adsorption/desorption, a pore distribution, a scanning electron microscopy, a transmission electron microscopy, an infrared spectrometry, a solid nuclear magnetic resonance spectrometry, etc. In addition, the adsorption of the metal ions may be determined by an ultraviolet/visible spectrometry, and an inductively coupled plasma emission spectrometry.

Hereinafter, exemplary embodiments in accordance with the present inventive concept will be described in detail. However, the present inventive concept is not limited to the following.

Example 1

Figure 6:
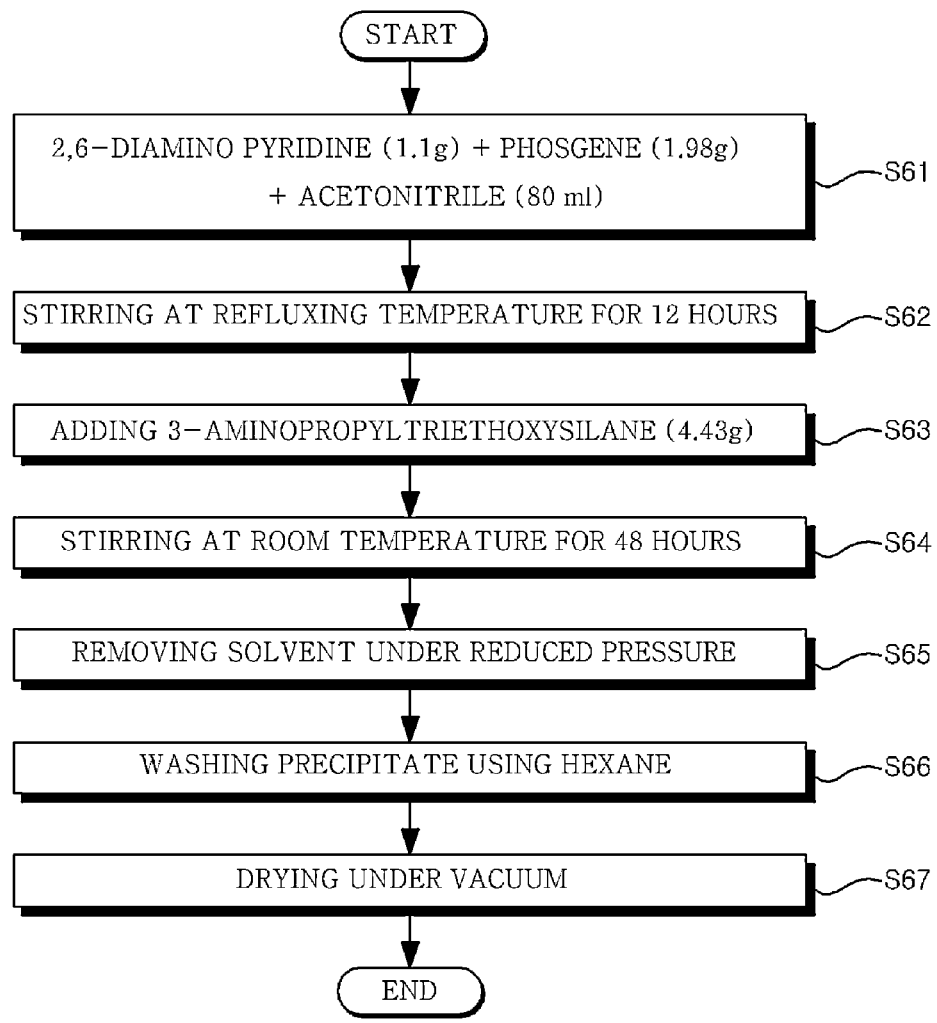
FIG. 6 is a flow chart for explaining a synthetic process of an organic-inorganic silica precursor including a 2,6-diamino pyridine group in accordance with exemplary embodiments of the present inventive concept.

Preparation of Organic-Inorganic Hybrid Silica Source Including Cross-Linked 2,6-Diamino Pyridine Group FIG. 6 is a flow chart for explaining a synthetic process of an organic-inorganic hybrid silica precursor including a cross-linked 2,6-diamino pyridine group in accordance with exemplary embodiments.

The synthetic process will be explained referring to FIG. 6. First, 1.1 g of 2,6-diamino pyridine and 1.98 g of phosgene are dissolved in 80 ml of acetonitrile (Step S61).

Then, the reactant is refluxed at a refluxing temperature of acetonitrile for 12 hours (Step S62). After that, 4.43 g of 3-aminopropyltriethoxysilane is added (Step S63).

The reactant is stirred at room temperature for 48 hours (Step S64), and then the solvent is removed under a reduced pressure (Step S65).

Precipitated material is washed using hexane (Step S66) and then dried under vacuum for 24 hours (Step S67).

Through performing the above-described processes, an organic-inorganic hybrid silica precursor including a cross-linked 2,6-diamino pyridine group is produced.

Figure 7:
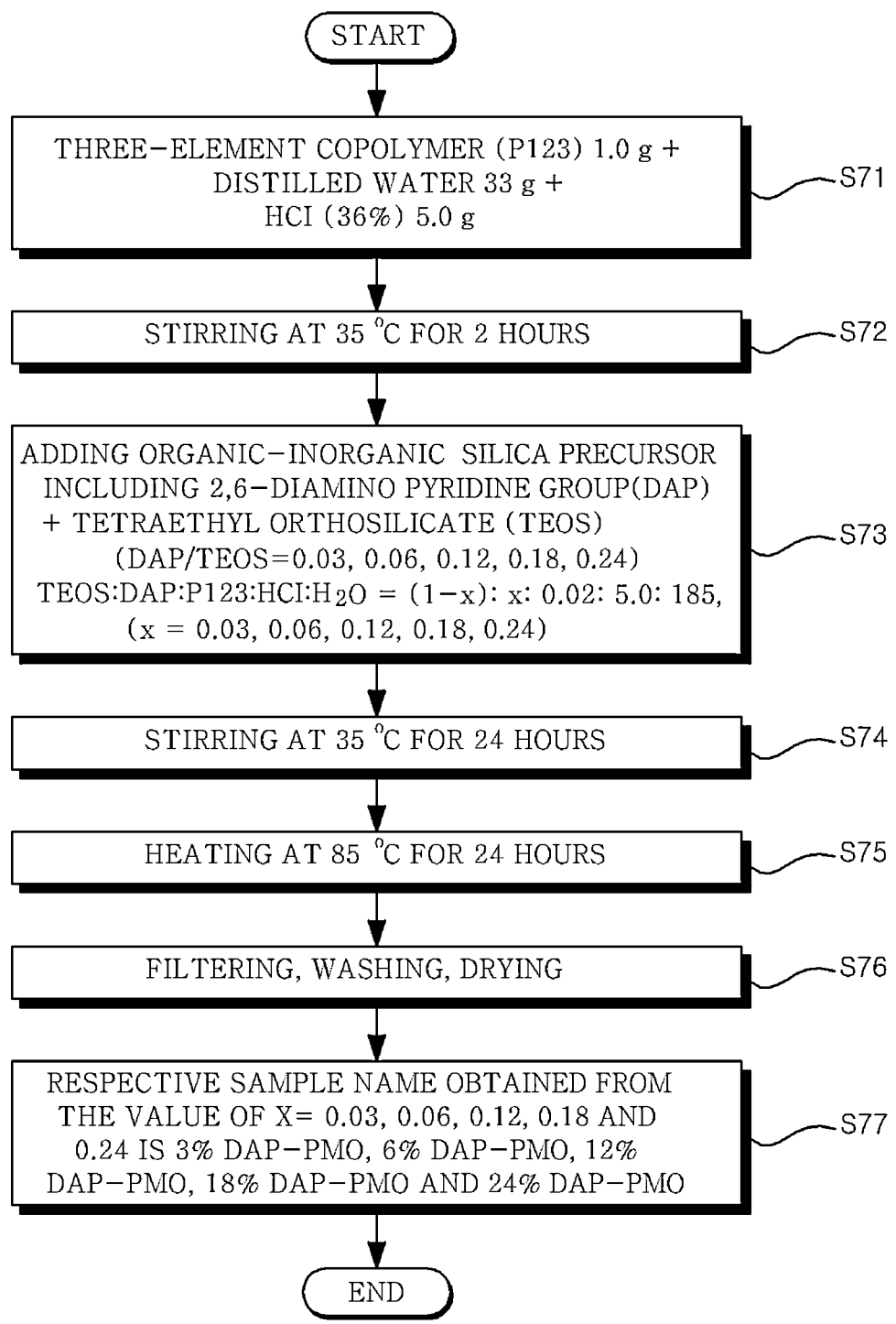
FIG. 7 is a flow chart for explaining a synthetic process of an organic-inorganic mesoporous silica/template hybrid material including a 2,6-diamino pyridine group.

Preparation of Organic-Inorganic Hybrid Mesoporous Silica/Template Hybrid Material Including Cross-Linked 2,6-Diamino Pyridine Group FIG. 7 is a flow chart for explaining a synthetic process of an organic-inorganic mesoporous silica/template hybrid material including a 2,6-diamino pyridine group.

1.0 g of P123, as a three-element copolymer is dissolved in 33.0 g of distilled water and 5.0 g of aqueous hydrochloric acid (36%) is added (Step S71). Then, thus obtained reactant is stirred at 35° C. for 2 hours (Step S72).

An organic-inorganic hybrid silica precursor including a cross-linked 2,6-diamino pyridine group (DAP) and tetraethyl orthosilicate (TEOS) are added into the reactant in various mixing ratios (Step S73). For example, the mixing ratios of DAP/TEOS are 0.03, 0.06, 0.12, 0.18 and 0.24. Accordingly, the final mixing ratios of the reacting materials of TEOS:DAP:P123: HCl:H$_2$O=(1-X):X:0.02:5.0:185 (X represents 0.03, 0.06, 0.12, 0.18 and 0.24).

The reactant is stirred at 35° C. for 24 hours (Step S74) and then heated at 80° C. for 24 hours (Step S75).

Then, filtering, washing and drying are performed (Step S76) to produce an organic-inorganic hybrid mesoporous silica/template hybrid material including a cross-linked 2,6-diamino pyridine group.

Figure 8:
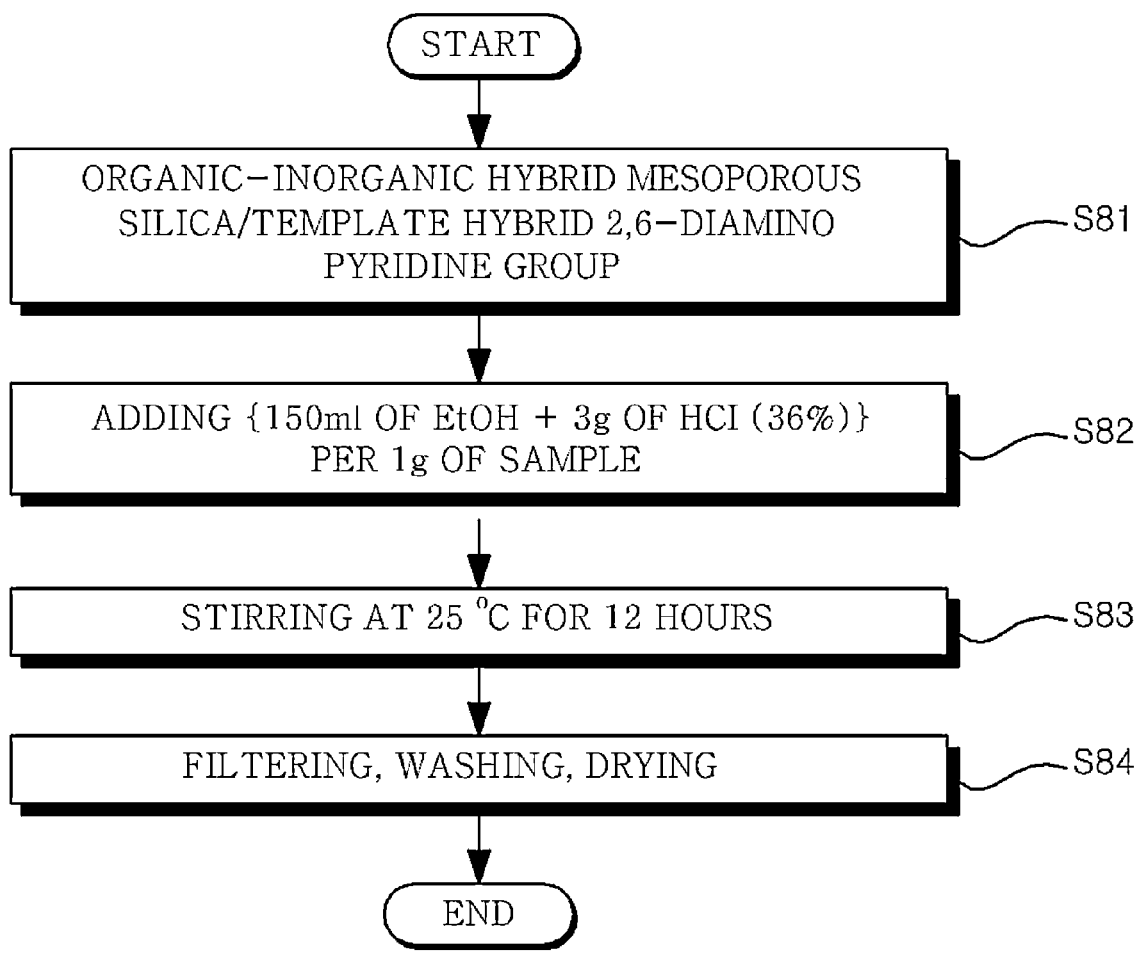
FIG. 8 is a flow chart for explaining a removing process of a template from an organic-inorganic hybrid mesoporous silica/template hybrid including a 2,6-amino pyridine group.

Removal of Template from Organic-Inorganic Hybrid Mesoporous Silica/Template Hybrid Material Including Cross-Linked 2,6-Diamino Pyridine Group FIG. 8 is a flow chart for explaining a removing process of a template from an organic-inorganic hybrid mesoporous silica/template hybrid material including a 2,6-amino pyridine group.

An ethanol (EtOH)-hydrochloric acid solution is added to an organic-inorganic hybrid mesoporous silica/template hybrid material including a 2,6-amino pyridine group. 150 ml of ethanol and 3 g of hydrochloric acid (aqueous solution of 36%) are used per 1 g of the organic-inorganic hybrid mesoporous silica/template hybrid material including the 2,6-amino pyridine group (Steps S81 & S82).

Then, the mixture is stirred at 25° C. for 12 hours (Step S83). Filtering, washing and drying are performed (Step S84) to produce an organic-inorganic hybrid mesoporous silica material including the 2,6-amino pyridine group in the porous wall and excluding the template.

Figure 9:
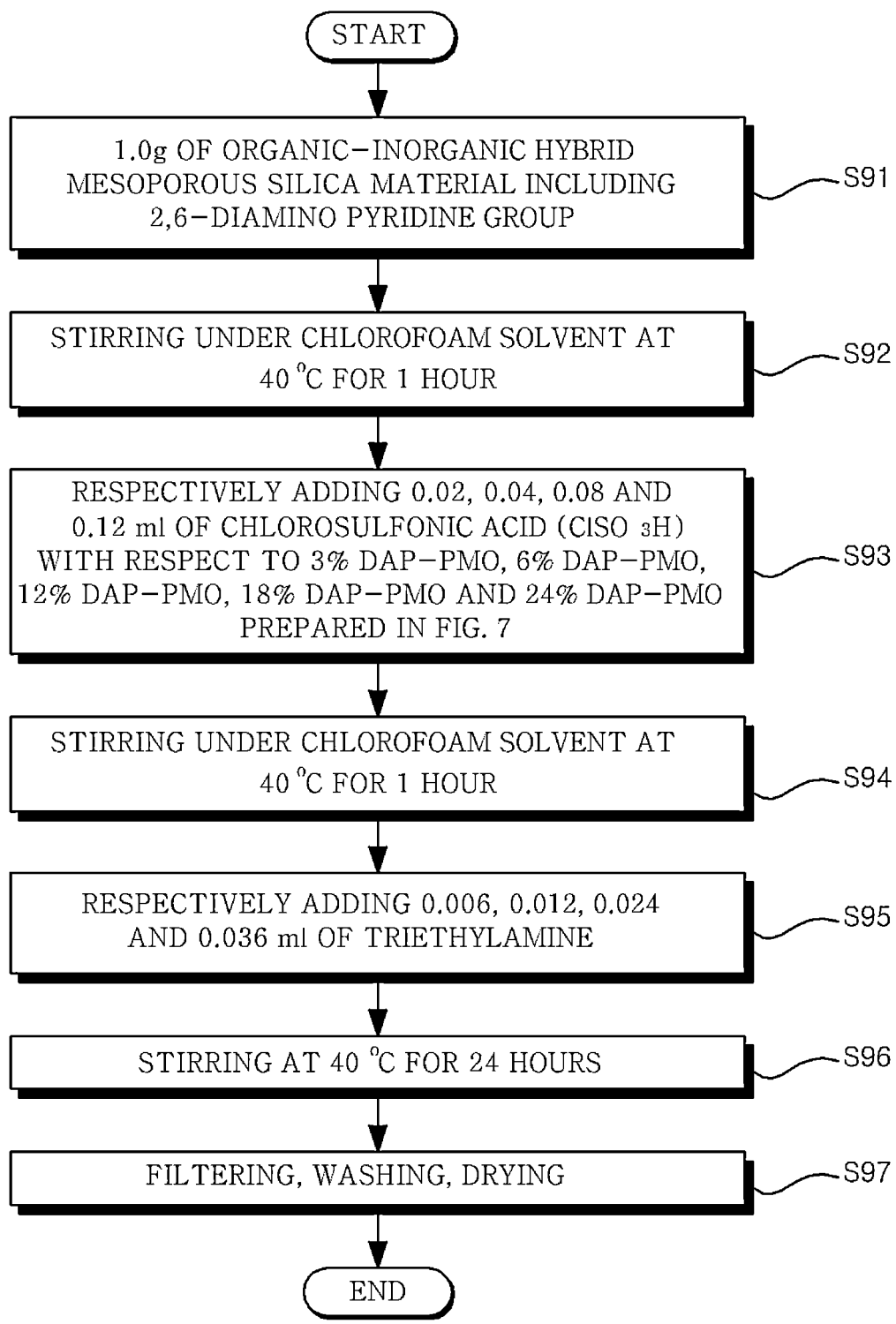
FIG. 9 is a flow chart for explaining a modifying process of an organic-inorganic hybrid mesoporous silica including a 2,6-diamino pyridine group by using a sulfonic acid group.

Preparation of Organic-Inorganic Hybrid Mesoporous Silica Material Modified by Sulfonic Acid Group FIG. 9 is a flow chart for explaining a modifying process of an organic-inorganic hybrid mesoporous silica including a 2,6-diamino pyridine group by using a sulfonic acid group.

1.0 g of an organic-inorganic hybrid mesoporous silica material including a 2,6-diamino pyridine group in a chloroform solvent is stirred at 40° C. for 1 hour (Steps S91 & S92).

Various amounts of chlorosulfonic acid (ClSO$_3$H) are added (Step S93). The amount of the chlorosulfonic acid may vary depending on the mixing ratio (DAP/TEOS) of the organic-inorganic hybrid silica precursor (DAP) and tetraethyl orthosilicate (TEOS). For example, is added 0.02 ml of the chlorosulfonic acid when DAP/TEOS=0.03, 0.04 ml of the chlorosulfonic acid when DAP/TEOS=0.06, 0.08 ml of the chlorosulfonic acid when DAP/TEOS=0.12, and 0.12 ml of the chlorosulfonic acid when DAP/TEOS=0.18.

After then, the reactant is stirred at 40° C. for 1 hour (Step S94), and various amounts of triethylamine is added (Step S95).

The amount of triethylamine may vary depending on the mixing ratio (DAP/TEOS). For example, is added 0.006 ml of triethylamine when DAP/TEOS=0.03, 0.012 ml of triethylamine when DAP/TEOS=0.06, 0.024 ml of triethylamine when DAP/TEOS=0.12, and 0.036 ml of triethylamine when DAP/TEOS=0.18.

Then, the reactant is stirred at 40° C. for 24 hours (Step S96), filtered, washed and dried (Step S97) to produce an organic-inorganic hybrid mesoporous silica material modified by a sulfonic acid group.

Figure 10:
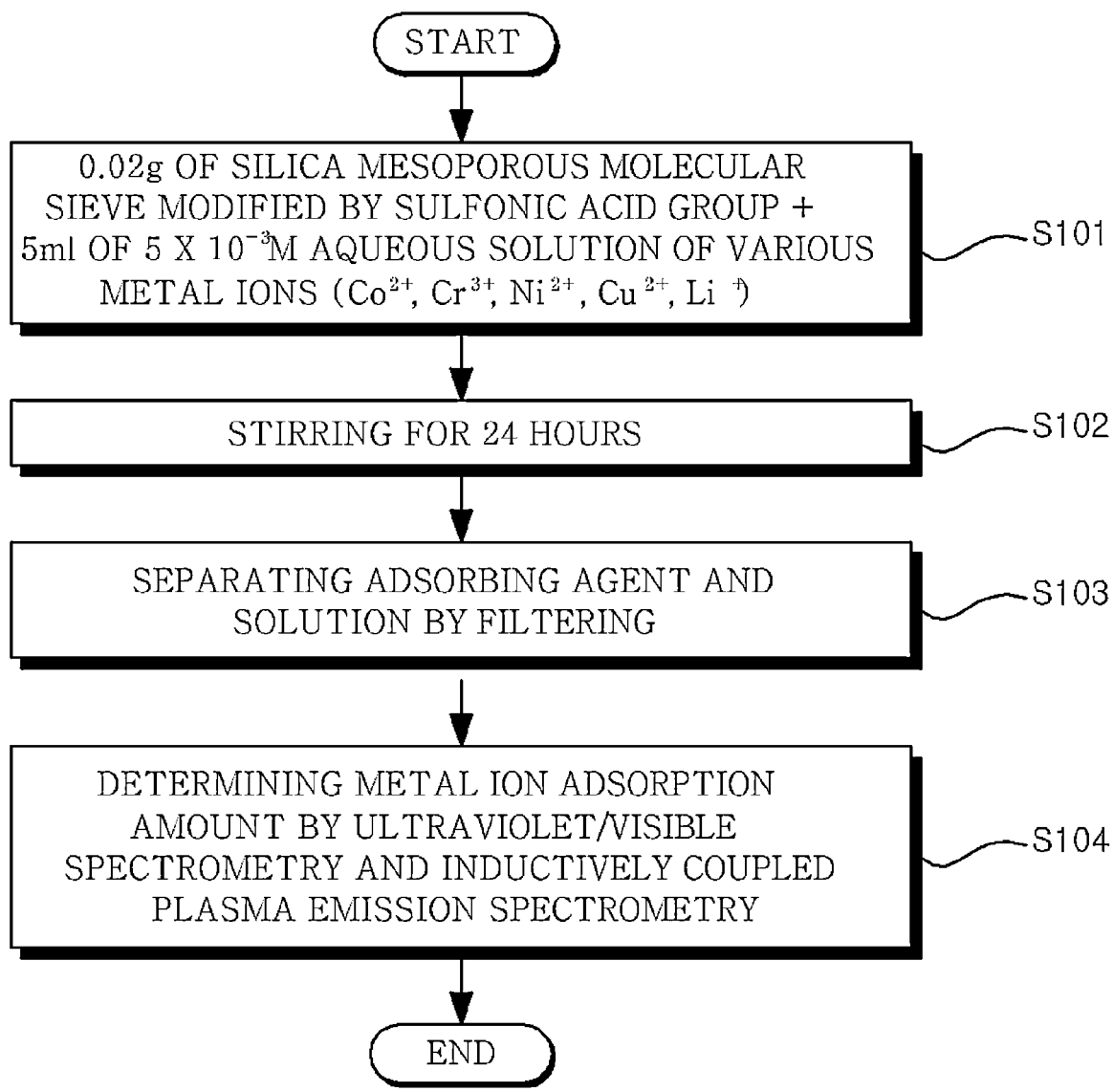
FIG. 10 is a flow chart for explaining an adsorbing process of metal ions using an organic-inorganic hybrid mesoporous silica material modified by a sulfonic acid group.

Adsorption of Metal Ions using Organic-Inorganic Hybrid Mesoporous Silica Material Modified by Sulfonic Acid Group FIG. 10 is a flow chart for explaining an adsorbing process of metal ions using an organic-inorganic hybrid mesoporous silica material modified by a sulfonic acid group.

Into 0.02 g of an organic-inorganic hybrid mesoporous silica material modified by a sulfonic acid group, 5 ml of an aqueous solution of 5×10$^{-3}$M of various metal ions (Co$^{2+}$, Cr$^{3+}$, Ni$^{2+}$, Cu$^{2+}$, Li$^+$) is added (Step S101).

After stirring for 12 hours (Step S102), an adsorbing agent and a solution are separated by means of a filtering method (Step S103). The separation is advantageously achieved by the filtering method.

Using the separated solution, an adsorption amount of metal ions are determined by an ultraviolet/visible spectrometry and an inductively coupled plasma emission spectrometry (Step S104).

Confirmation and Evaluation of Product Material

The pore structure, the pore size, the particle shape and the constituting material of the porous wall of an intermediate material obtained through the synthesis and the organic-inorganic hybrid mesoporous silica material including a modified organic group by the sulfonic acid group in the porous wall, are analyzed by an X-ray diffraction pattern, a nitrogen isothermal adsorption/desorption, a pore distribution, a scanning electron microscopy, a transmission electron microscopy, an infrared spectrometry, a solid nuclear magnetic resonance spectrometry, etc. In addition the adsorption of metal ions is determined using an ultraviolet/visible spectrometry and an inductively coupled plasma emission spectrometry.

Figure 11:
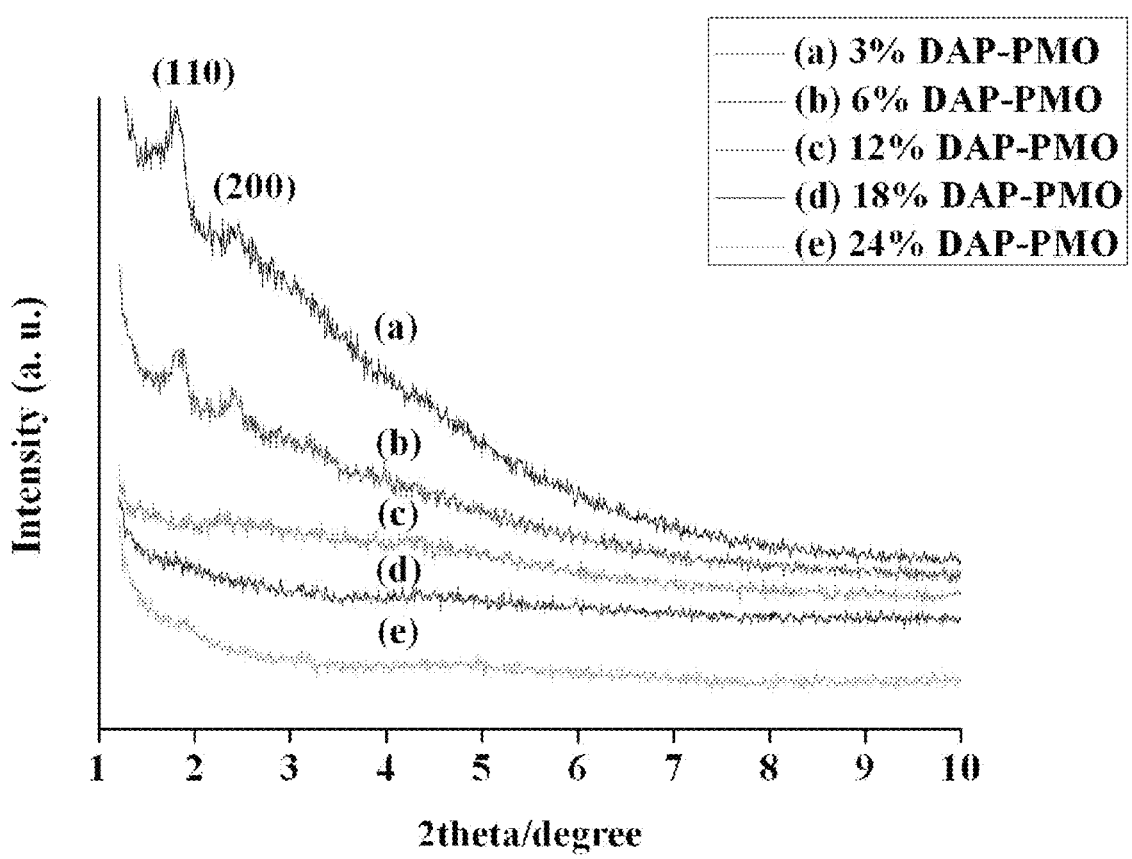
FIG. 11 illustrates graphs of X-ray diffraction patterns of organic-inorganic hybrid mesoporous silica materials in which an organic-inorganic silica precursor including a 2,6-diamino pyridine group is included with different mixing ratios of DAP/TEOS, including (a) 0.03 (3% DAP-PMO), (b) 0.06 (6% DAP-PMO), (c) 0.12 (12% DAP-PMO), (d) 0.18 (18% DAP-PMO), and (e) 0.24 (24% DAP-PMO).

FIG. 11 illustrates graphs of X-ray diffraction patterns of organic-inorganic hybrid mesoporous silica materials in which an organic-inorganic silica precursor including a 2,6-diamino pyridine group is included in different mixing ratios.

Here, the mixing ratios of DAP/TEOS include (a) 0.03 (3% DAP-PMO) (b) 0.06 (6% DAP-PMO), (c) 0.12 (12% DAP-PMO), (d) 0.18 (18% DAP-PMO), and (e) 0.24 (24% DAP-PMO).

Referring to the result, the organic-inorganic hybrid mesoporous silica material including a 2,6-diamino pyridine precursor at the lowest ratio (2,6-diamino pyridine (DAP)/tetraethyl orthosilicate (TEOS)=0.03) illustrates specific peaks of (110) and (200), which are typical for a hexahedral structure. This result means that medium size pores are arranged in regular and have a hexahedral structure.

As the mixing ratio of the 2,6-diamino pyridine precursor increases and DAP/TEOS=0.24, the intensity of the X-ray diffraction pattern is decreased. As the organic-inorganic hybrid silica precursor having a long alkyl chain is mixed into the porous wall, the hexahedral porous arrangement structure gradually collapses.

Well arranged hexahedral porous structure may be obtained until when increasing the mixing ratio of DAP/TEOS to 0.12.

Figure 12:
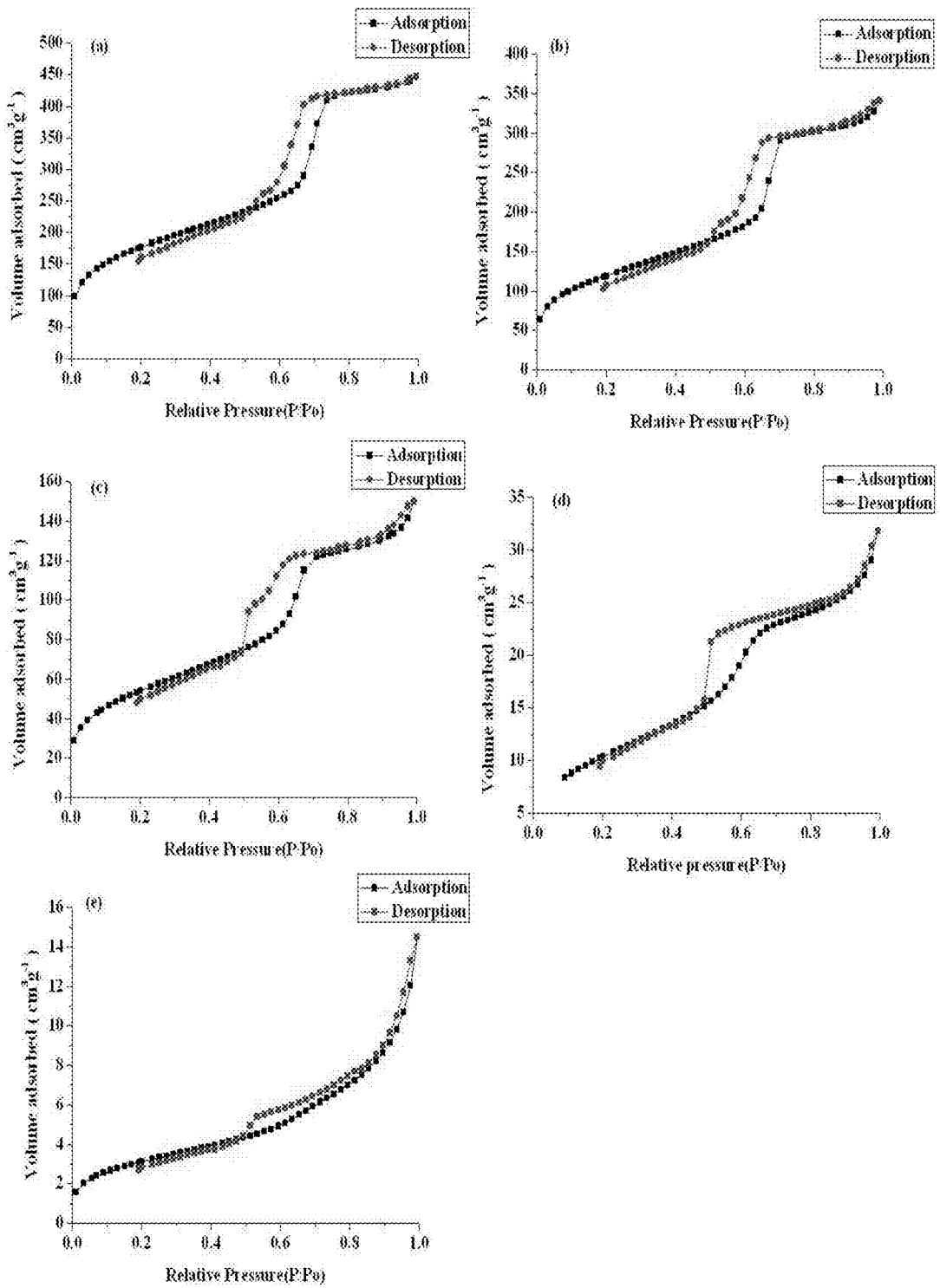
FIG. 12 illustrates graphs of nitrogen isothermal adsorption/desorption of organic-inorganic hybrid mesoporous silica materials in which an organic-inorganic silica precursor including a 2,6-diamino pyridine group is included with different mixing ratios of DAP/TEOS, including (a) 0.03 (3% DAP-PMO), (b) 0.06 (6% DAP-PMO), (c) 0.12 (12% DAP-PMO), (d) 0.18 (18% DAP-PMO), and (e) 0.24 (24% DAP-PMO).

In the graph of nitrogen isothermal adsorption/desorption (graph c) in FIG. 12, a rapid increase of nitrogen adsorption is illustrated at a relative pressure (P/P$_0$) within a range of about 0.5~0.7. From the result, it is known that a pore structure includes well arranged medium size pores.

As shown in X-ray diffraction patterns in graphs (d) and (e), the samples having the DAP/TEOS mixing ratios of 0.18 and 0.24 also have the pore structure having the medium size pores. However, the regularity of the pore structure is lower than that obtained when the DAP/TEOS mixing ratio is 0.12 or less.

FIG. 12 illustrates graphs of nitrogen isothermal adsorption/desorption of organic-inorganic hybrid mesoporous silica materials in which an organic-inorganic silica precursor including a 2,6-diamino pyridine group is included with different mixing ratios of DAP/TEOS including (a) 0.03 (3%

DAP-PMO), (b) 0.06 (6% DAP-PMO), (c) 0.12 (12% DAP-PMO), (d) 0.18 (18% DAP-PMO), and (e) 0.24 (24% DAP-PMO).

The nitrogen isothermal adsorption/desorption graphs for the organic-inorganic hybrid mesoporous silica materials (DAP-PMOs) including 2,6-diamino pyridine precursors of which DAP/TEOS ratio is 0.03, 0.06 and 0.12 (that is, 3% DAP—PMO, 6% DAP-PMO and 12% DAP-PMO, respectively) illustrate a rapid increasing phenomenon of a nitrogen adsorption amount within a relative pressure ($P/P_0$) range of about 0.4~0.7. From the result, it is confirmed that the silica material is typical mesoporous material.

Figure 13:
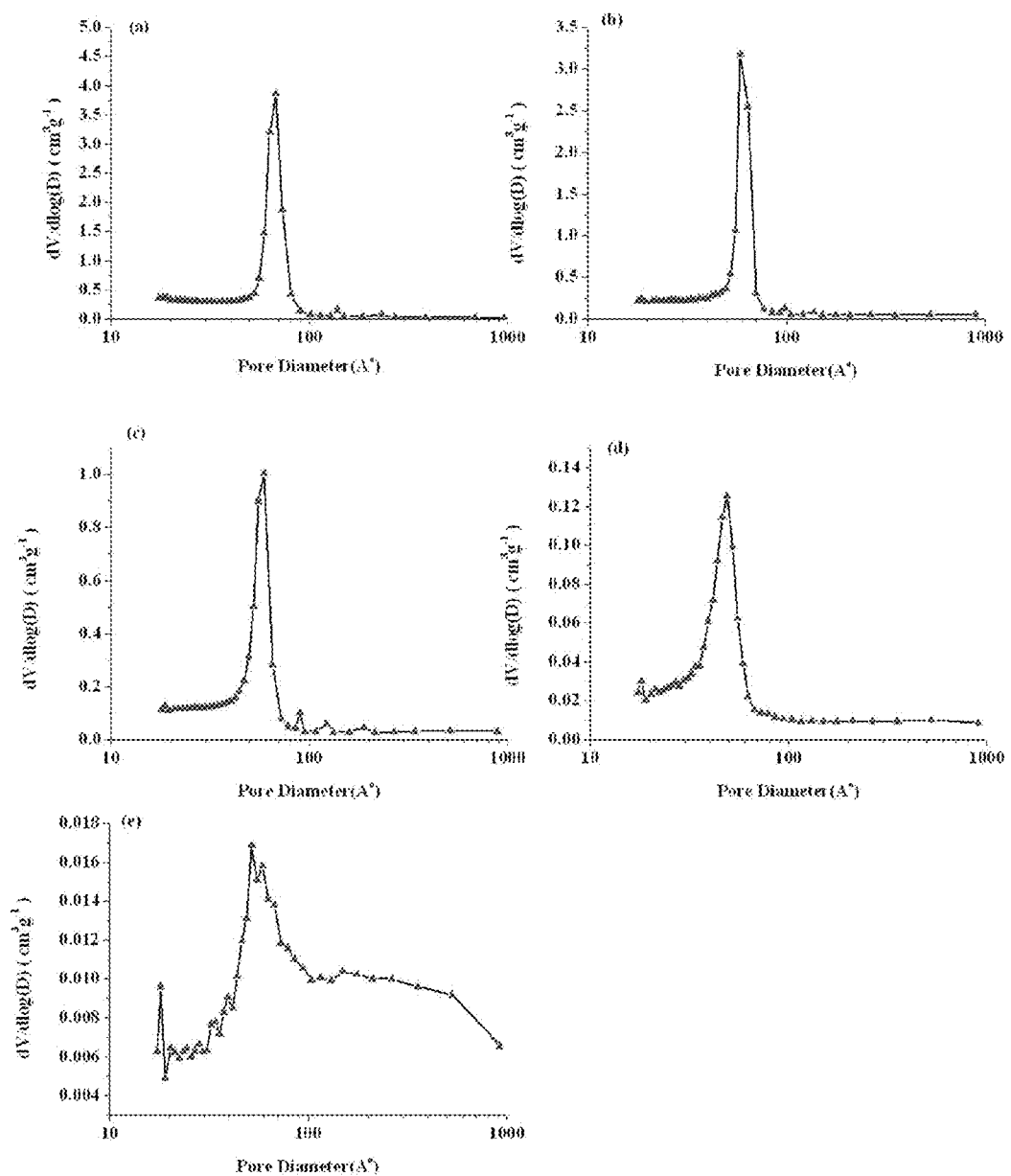
FIG. 13 illustrates graphs of pore distribution of organic-inorganic hybrid mesoporous silica materials in which an organic-inorganic silica precursor including a 2,6-diamino pyridine group is included with different mixing ratios of DAP/TEOS, including (a) 0.03 (3% DAP-PMO), (b) 0.06 (6% DAP-PMO), (c) 0.12 (12% DAP-PMO), (d) 0.18 (18% DAP-PMO), and (e) 0.24 (24% DAP-PMO).
Figures 14, 15:
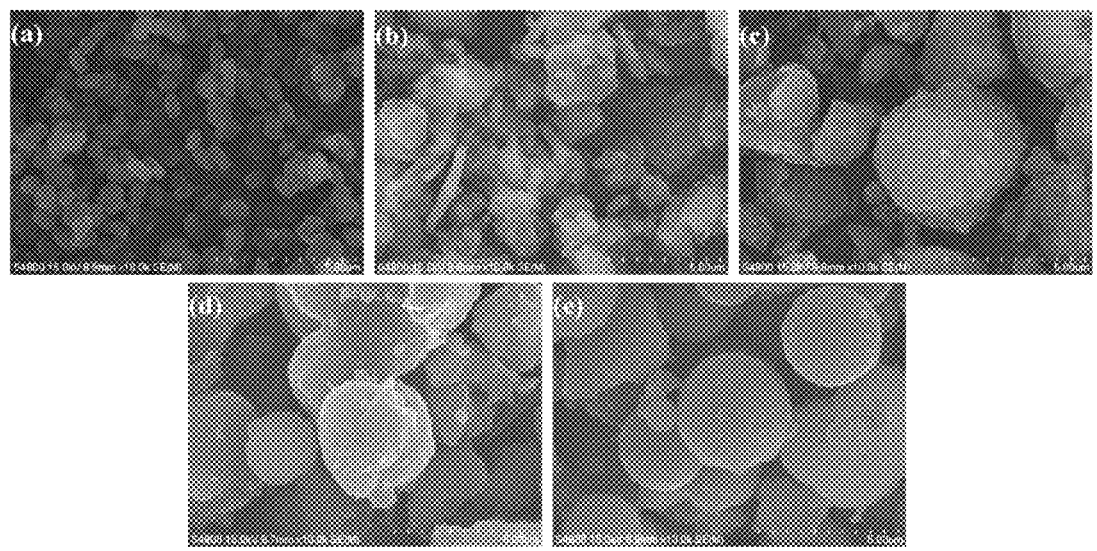
FIG. 14 is a table illustrating values on structural properties of DAP-PMO including different amounts of a 2,6-diamino pyridine group.
FIG. 15 illustrates SEM (scanning electron microscopy) drawings of organic-inorganic hybrid mesoporous silica materials in which an organic-inorganic silica precursor including a 2,6-diamino pyridine group is included with different mixing ratios of DAP/TEOS, including (a) 0.03 (3% DAP-PMO), (b) 0.06 (6% DAP-PMO), (c) 0.12 (12% DAP-PMO), (d) 0.18 (18% DAP-PMO), and (e) 0.24 (24% DAP-PMO).

FIG. 13 illustrates graphs of a pore distribution of organic-inorganic hybrid mesoporous silica materials in which an organic-inorganic silica precursor including a 2,6-diamino pyridine group is included with different mixing ratios of DAP/TEOS. FIG. 14 is a table illustrating values on structural properties of DAP-PMO including different amounts of a 2,6-diamino pyridine group.

Referring to FIG. 13, graphs (a), (b) and (c) illustrate a narrow pore distribution and a specific pore size. Referring to FIG. 14, for the samples of which ratios of DAP/TEOS are 0.03, 0.06 and 0.12 (that is, 3% DAP-PMO, 6% DAP-PMO and 12% DAP-PMO, respectively), the pore seize is respectively 43 Å, 49 Å and 48 Å and the surface area is respectively 637 m$^2$/g, 432 m$^2$/g and 196 m$^2$/g. In addition, when the DAP/TEOS ratio increases to 0.18 (18% DAP-PMO) and 0.24 (24% DAP-PMO), the pore size increases to 52 Å and 58 Å respectively, and the surface area decreases to 38 m$^2$/g and 12 m$^2$/g.

Referring to FIG. 14, as the amount of the 2,6-diamino pyridine precursor increases, the pore volume decreases from 0.69 cm$^2$/g to 0.02 cm$^2$/g. This result is obtainable since the regularity of the pore arrangement is lowered as the amount of the 2,6-diamino pyridine precursor in the porous wall increases.

FIG. 15 illustrates SEM (scanning electron microscopy) drawings of organic-inorganic hybrid mesoporous silica materials in which an organic-inorganic silica precursor including a 2,6-diamino pyridine group is included with different mixing ratios of DAP/TEOS, including (a) 0.03 (3% DAP-PMO), (b) 0.06 (6% DAP-PMO), (c) 0.12 (12% DAP-PMO), (d) 0.18 (18% DAP-PMO), and (e) 0.24 (24% DAP-PMO).

The particle shape of the mesoporous material is a hexagonal plate shape when the amount of the organic-inorganic precursor including the 2,6-diamino pyridine group, that is, DAP/TEOS=0.06 (6% DAP-PMO) or less. See graphs (a) and (b) in FIG. 15. On the contrary, when the amount increases to DAP/TEOS=0.24 (24% DAP-PMO), the particle shape changes from the hexagonal plate shape to a globular shape. See graphs (c), (d) and (e) in FIG. 15. That is, the particle shape changes from the hexagonal plate shape to the globular shape as the DAP/TEOS ratio increases.

Figure 16:
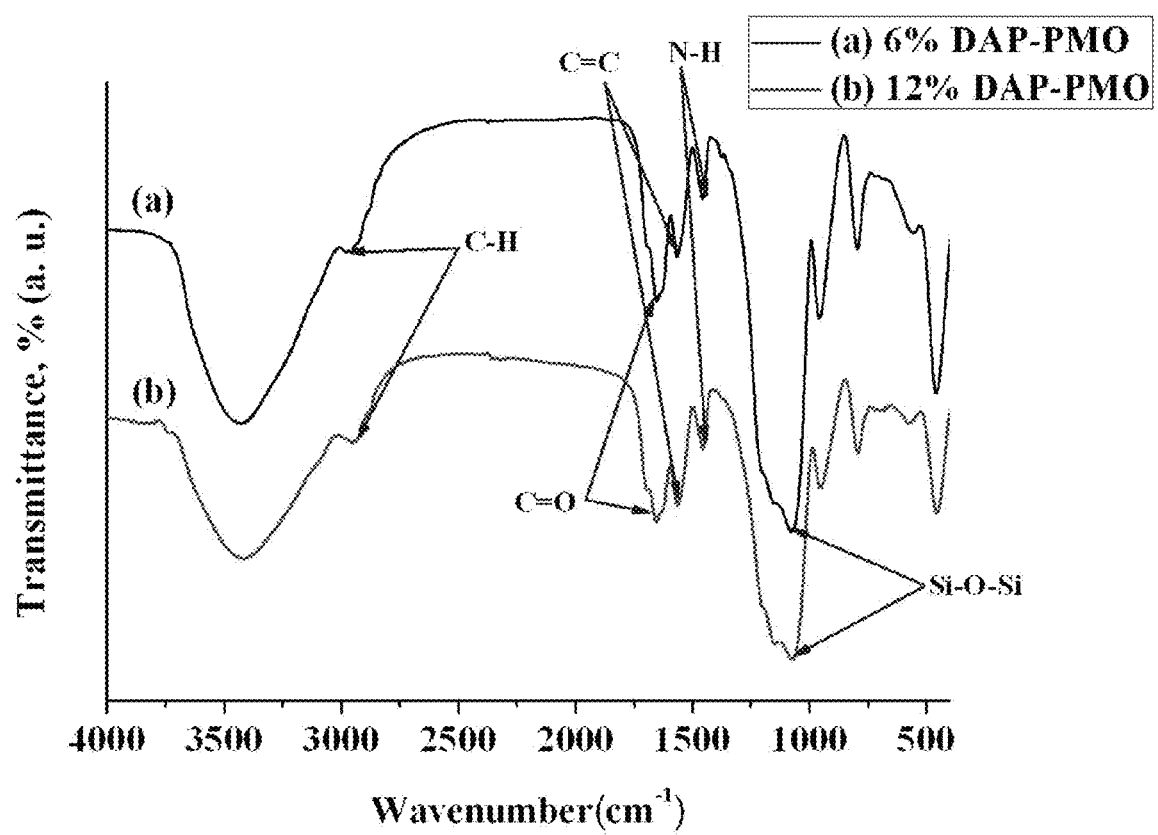
FIG. 16 illustrates infrared spectra of organic-inorganic hybrid mesoporous silica materials in which an organic-inorganic silica precursor including a 2,6-diamino pyridine group is included with different mixing ratios of DAP/TEOS, including (a) 0.03 (3% DAP-PMO) and (b) 0.06 (6% DAP-PMO).

FIG. 16 illustrates infrared spectra of organic-inorganic hybrid mesoporous silica materials in which an organic-inorganic silica precursor including a 2,6-diamino pyridine group is included with different mixing ratios of DAP/TEOS, including (a) 0.03 (3% DAP-PMO) and (b) 0.06 (6% DAP-PMO).

As the 2,6-diamino pyridine organic group is mixed into the porous wall, the following specific peaks are illustrated.

(a) 0.06 (6% DAP-PMO):C—H(2956 cm$^{-1}$), C=O (1653 cm$^{-1}$), C=C (1565 cm$^{-1}$), N—H (1455 cm$^{-1}$), Si—O—Si (1077 cm$^{-1}$, 794 cm$^{-1}$, 458 cm$^{-1}$), Si—OH (957 cm$^{-1}$), (b) 0.12 (12% DAP-PMO):C—H(2952 cm$^{-1}$), C=O (1653 cm$^{-1}$), C=C (1563 cm$^{-1}$), N—H (1455 cm$^{-1}$), Si—O—Si (1073 cm$^{-1}$, 793 cm$^{-1}$, 456 cm$^{-1}$), Si—OH (952 cm$^{-1}$).

From the above-described result, it would be known that the organic-inorganic silica precursor including the 2,6-diamino pyridine group is successfully mixed into the porous wall.

FIGS. 17A and 17B are NMR spectra of (a) $^{29}$Si and (b) $^{13}$C on an organic-inorganic hybrid mesoporous silica material (12% DAP-PMO) including a 2,6-diamino pyridine group. Referring to the $^{29}$Si solid nuclear magnetic resonance spectrum in FIG. 17A, $Q^n$ species illustrated by silica ($Q^n$=Si (OSO$_n$(OH)$_{4-n}$, n=2, 3, 4) ($Q^4$:−109.7 ppm, $Q^3$:−101.3 ppm, $Q^2$:−92.7 ppm) and $T^m$ species illustrated by the organic-inorganic hybrid precursor including an organic group ($T^m$=RSi(OSi)$_m$(OEt)$_{3-m}$, m=2, 3) ($T^2$:−57 ppm,:$T^3$:−66 ppm) are shown. Referring to $^{13}$C solid nuclear magnetic resonance spectrum in FIG. 17B, specific peaks are shown at 22.1 ppm, 43.6 ppm, 57.8 ppm, 96.3 ppm, 146.1 ppm, 155.5 ppm and 164.9 ppm. From the result, it also could be known that the organic-inorganic silica precursor including the 2,6-diamino pyridine group is successfully included in the porous wall.

The presence of the cross-linked 2,6-diamino pyridine group within the organic-inorganic hybrid mesoporous silica wall may be confirmed from the analyzed results of the X-ray diffraction pattern, the nitrogen isothermal adsorption/desorption, the pore distribution, the scanning electron microscopy, the infrared spectrometry and the $^{29}$Si and $^{13}$C solid nuclear magnetic resonance spectra.

Figure 18:
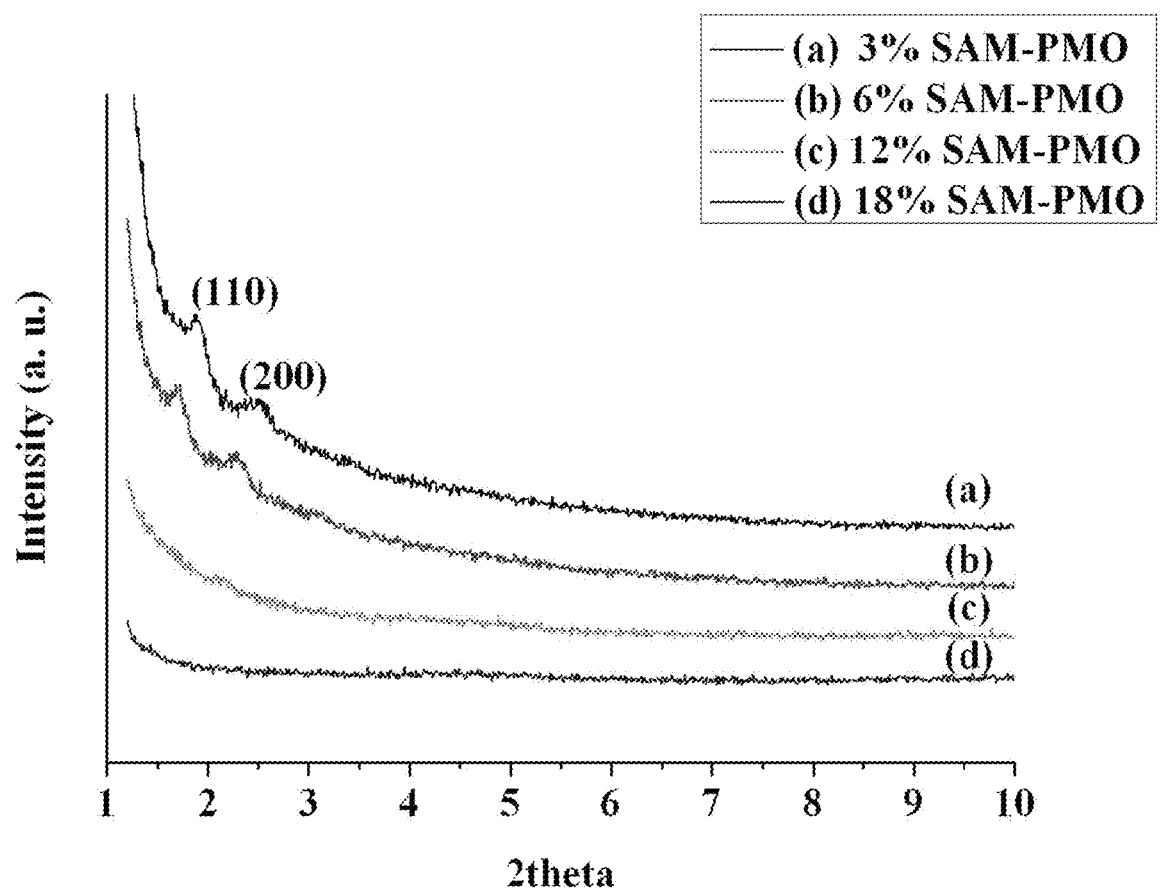
FIG. 18 illustrates X-ray diffraction patterns of sulfonic acid group modified organic-inorganic hybrid mesoporous silica materials including (a) 3% SAM-PMO, (b) 6% SAM-PMO, (c) 12% SAM-PMO, and (d) 18% SAM-PMO, respectively from 3% DAP-PMO, 6% DAP-PMO, 12% DAP-PMO and 18% DAP-PMO.

FIG. 18 illustrates X-ray diffraction patterns of sulfonic acid group modified organic-inorganic hybrid mesoporous silica materials with respect to each of 3% DAP-PMO, 6% DAP-PMO, 12% DAP-PMO and 18% DAP-PMO.

Here, the samples are (a) 3% SAM-PMO, (b) 6% SAM-PMO, (c) 12% SAM-PMO, and (d) 18% SAM-PMO.

Peaks having a narrow peak width and properly separated specific peaks of (110) and (200) are illustrated for each sample. Form the result, it would be shown that medium size pores are arranged in very regular hexahedral structure. However, the mesoporous silica material modified by the sulfonic acid group illustrates an X-ray diffraction pattern having a lower intensity than that of the mesoporous silica material before modification by the sulfonic acid group as illustrated in FIG. 11. This result is obtainable not because the collapse of the arrangement of the hexahedral structure but because the presence of the sulfonic acid group at the surface of and in the pores to lower a contrast of the porous wall and the pores. When considering the result, the modification by the sulfonic acid group in the pores is performed well.

Figure 19:
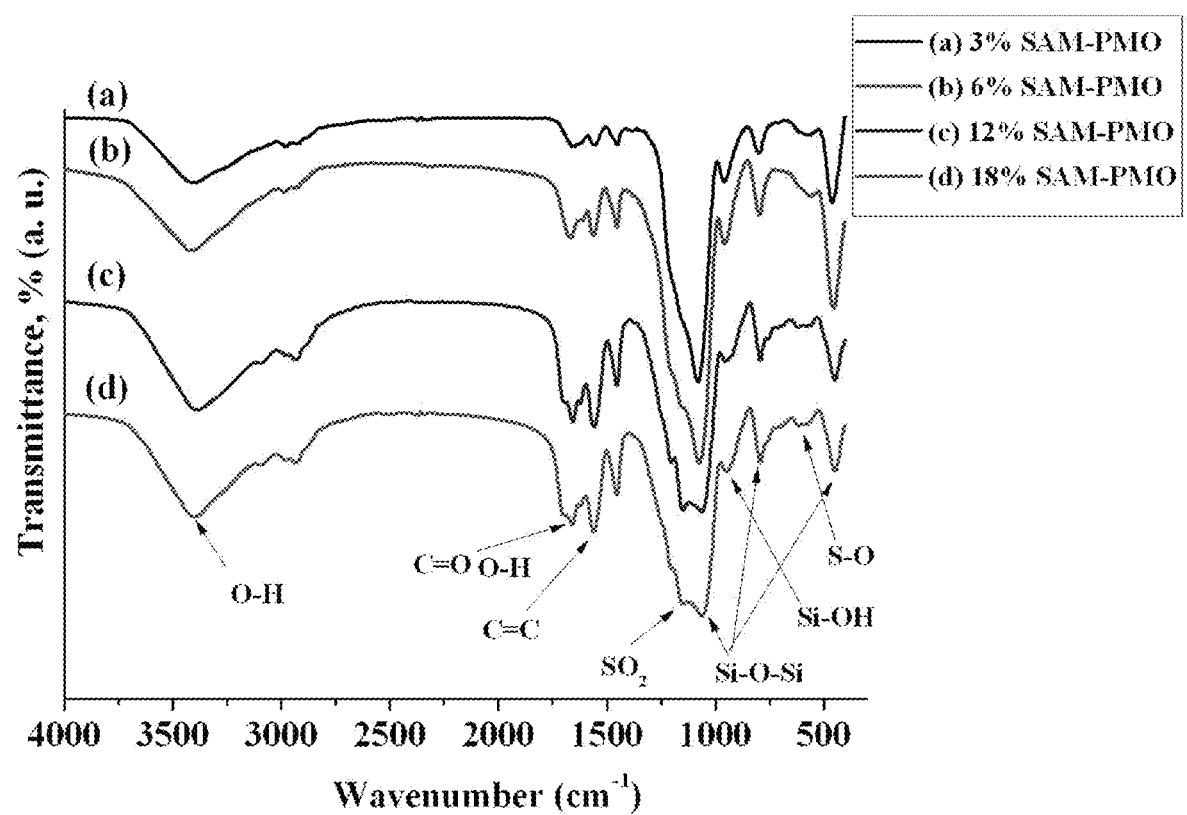
FIG. 19 illustrates infrared spectra of sulfonic acid group modified organic-inorganic hybrid mesoporous silica materials including (a) 3% SAM-PMO, (b) 6% SAM-PMO, (c) 12% SAM-PMO, and (d) 18% SAM-PMO.

FIG. 19 illustrates infrared spectra of sulfonic acid group modified organic-inorganic hybrid mesoporous silica materials such as (a) 3% SAM-PMO, (b) 6% SAM-PMO, (c) 12% SAM-PMO, and (d) 18% SAM-PMO.

According to the modification by the sulfonic acid group, the peak intensity around 1150 cm$^{-1}$ is increased. This is due to an O=S=O group included in the sulfonic acid group. In addition, a specific peak around 583 cm$^{-1}$ is illustrated due to an S—O group included in the sulfonic acid group. When considering the infrared spectrum result, the formation of the sulfonic acid group at the surface portion of and within the pores may be confirmed.

Figure 20:
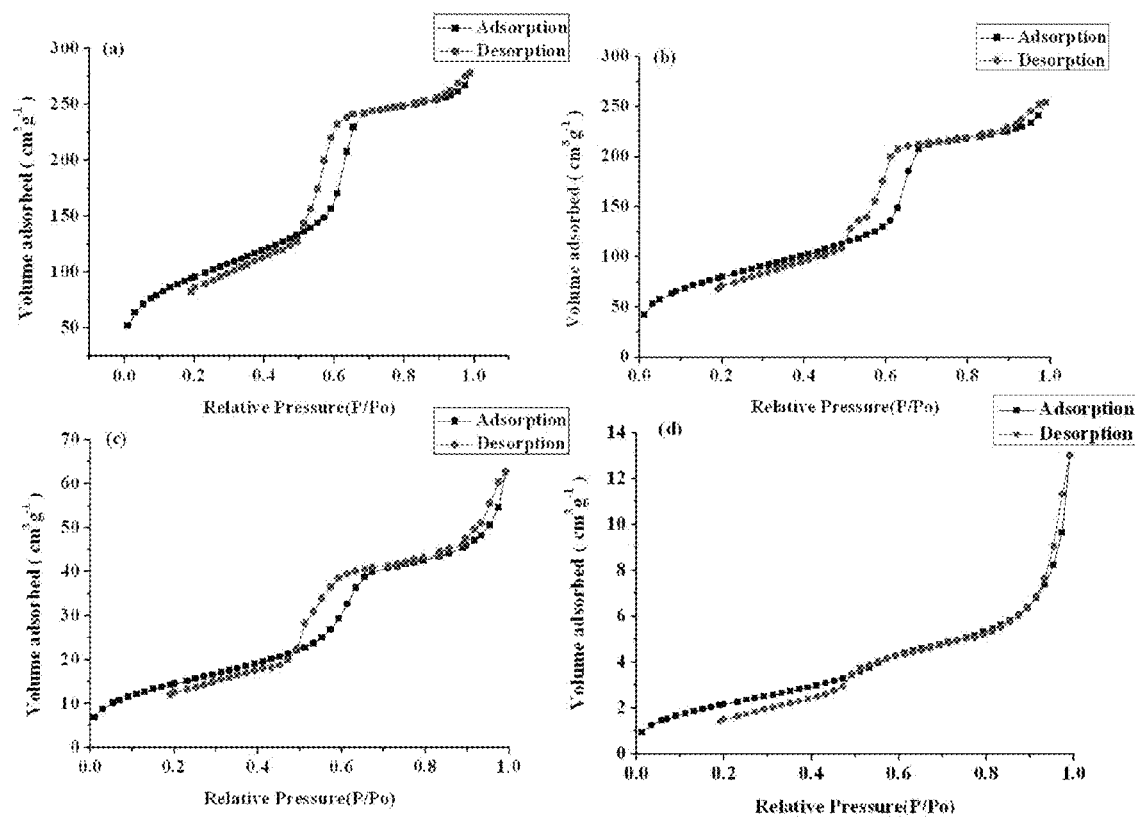
FIG. 20 illustrates nitrogen isothermal adsorption/desorption graphs of sulfonic acid group modified organic-inorganic hybrid mesoporous silica materials including (a) 3% SAM-PMO, (b) 6% SAM-PMO, (c) 12% SAM-PMO, and (d) 18% SAM-PMO.

FIG. 20 illustrates nitrogen isothermal adsorption/desorption graphs of sulfonic acid group modified organic-inorganic hybrid mesoporous silica materials such as (a) 3% SAM-PMO, (b) 6% SAM-PMO, (c) 12% SAM-PMO, and (d) 18% SAM-PMO.

Organic-inorganic hybrid mesoporous silica materials modified by the sulfonic acid group such as 3% SAM-PMO, 6% SAM-PMO, 12% SAM-PMO, and 18% SAM-PMO illustrate a rapid increasing phenomenon of a nitrogen adsorption amount at a relative pressure ($P/P_0$) in a range of about 0.4~0.7. From the result, it would be shown that the mesoporous material after being modified by the sulfonic acid group also is a typical mesoporous material.

Figure 21:
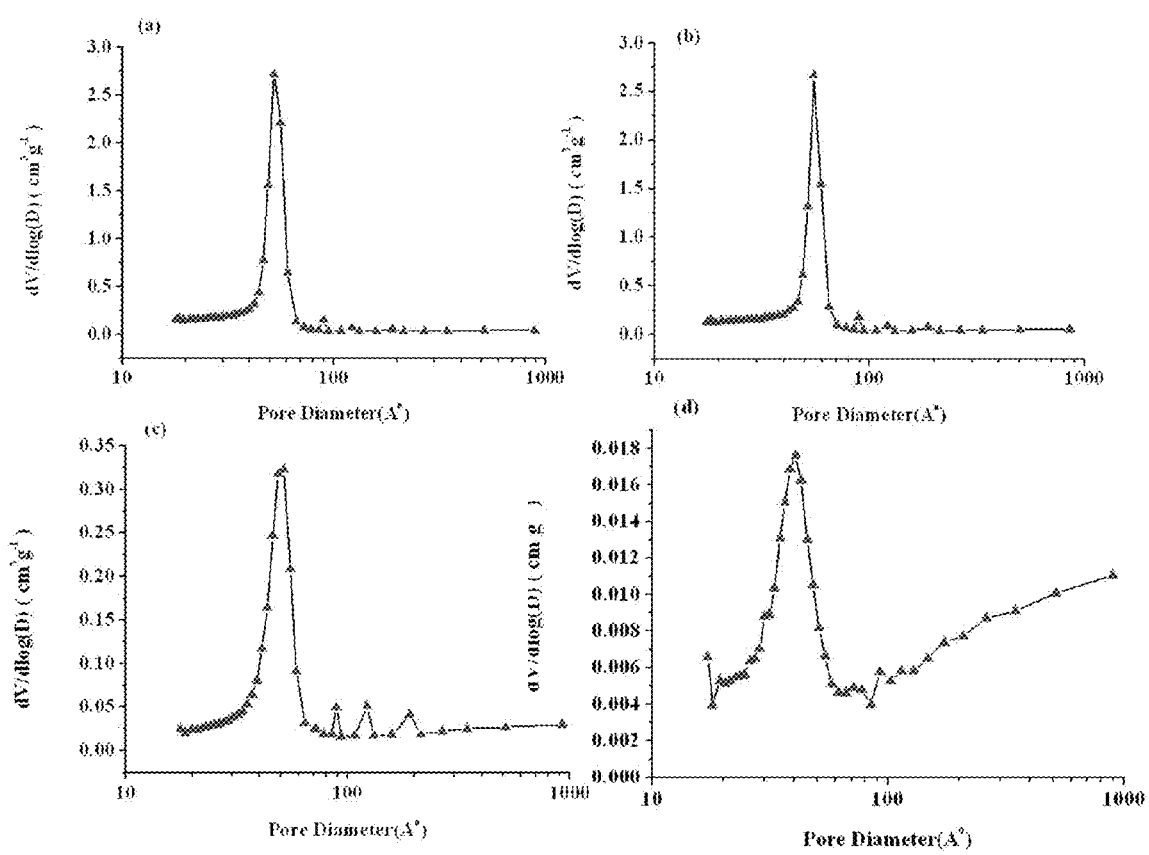
FIG. 21 illustrates graphs of a pore distribution of sulfonic acid group modified organic-inorganic hybrid mesoporous silica materials including (a) 3% SAM-PMO, (b) 6% SAM-PMO, (c) 12% SAM-PMO, and (d) 18% SAM-PMO.
Figures 22, 23:
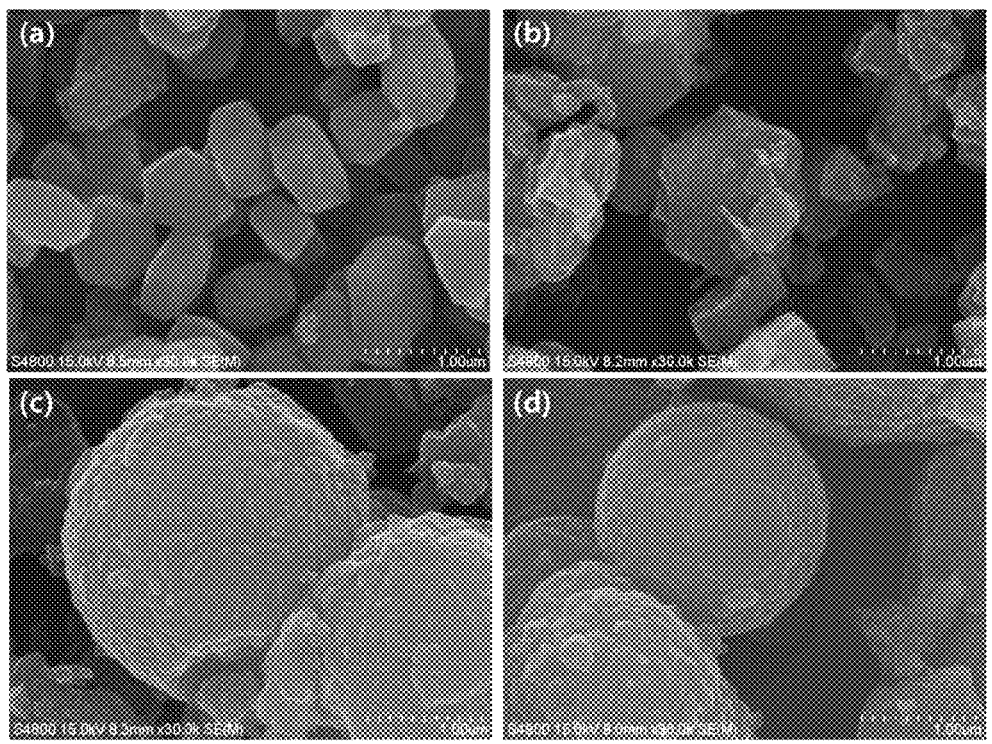
FIG. 22 is a table illustrating values on structural properties of SAM-PMO obtained by using different amounts of chlorosulfonic acid.
FIG. 23 illustrates SEM drawings of sulfonic acid group modified organic-inorganic hybrid mesoporous silica materials including (a) 3% SAM-PMO, (b) 6% SAM-PMO, (c) 12% SAM-PMO, and (d) 18% SAM-PMO.

FIG. 21 illustrates graphs of pore distributions of sulfonic acid group modified organic-inorganic hybrid mesoporous silica materials such as (a) 3% SAM-PMO, (b) 6% SAM-PMO, (c) 12% SAM-PMO, and (d) 18% SAM-PMO. FIG. 22 is a table illustrating values on structural properties of SAM-PMO of different content amounts. Narrow pore distribution and specific pore size may be obtainable for each of the samples.

Referring to FIG. 22, the pore size is 49 Å, 51 Å, 53 Å and 54 Å, and the surface area is 348 m$^2$/g, 292 m$^2$/g, 64 m$^2$/g and 18 m$^2$/g, respectively for 3% SAM-PMO, 6% SAM-PMO, 12% SAM-PMO and 18% SAM-PMO modified by the sulfonic acid group. As the amount of the modified organic group (sulfonic acid group) increases, the pore volume decreases from about 0.43 cm$^2$/g to about 0.02 cm$^2$/g. The surface area of the mesoporous silica material modified by the sulfonic acid group is relatively small when compared to that of the mesoporous silica material before modifying using the sulfonic acid group (DAP-PMO) as illustrated in FIG. 14. When considering the result, it would be known that the modification using the sulfonic acid group within the mesoporous is performed well.

FIG. 23 illustrates SEM drawings of sulfonic acid group modified organic-inorganic hybrid mesoporous silica materials such as 3% SAM-PMO, 6% SAM-PMO, 12% SAM-PMO, and 18% SAM-PMO. In FIG. 23, (a) corresponds to 3% SAM-PMO, (b) corresponds to 6% SAM-PMO, (c) corresponds to 12% SAM-PMO, and (d) corresponds to 18% SAM-PMO.

Just like the mesoporous silica material before the modification using the sulfonic acid group, the particle shape of the mesoporous silica material modified by the sulfonic acid group is changed from a hexagonal plate shape to a globular shape in accordance with an increase of DAP/TEOS ratio.

Figure 24:
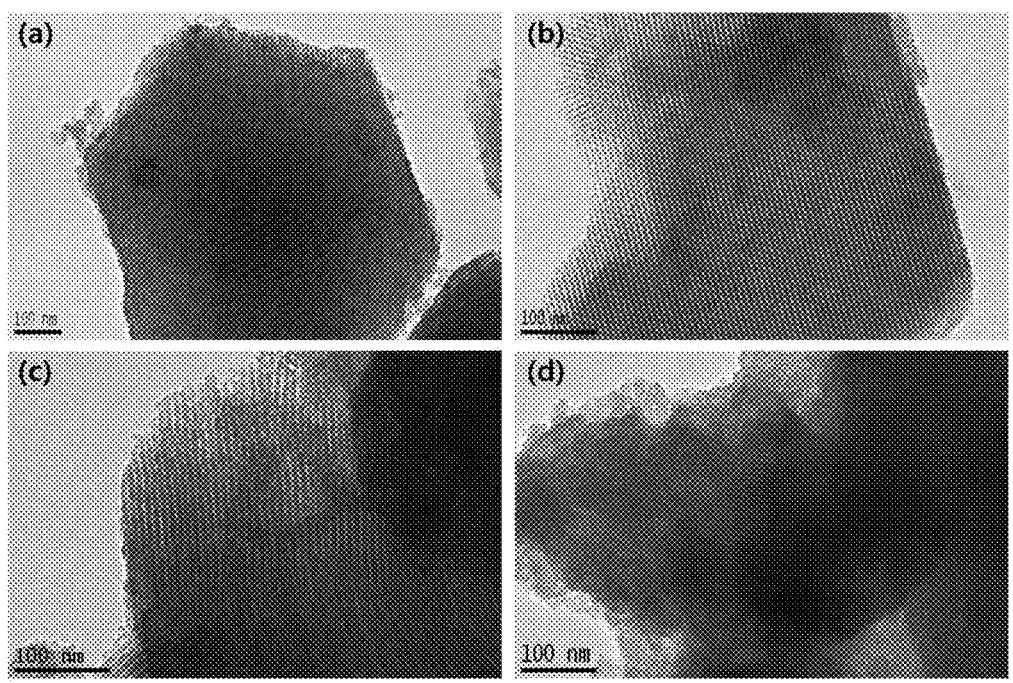
FIG. 24 illustrates TEM (transmission electron microscopy) drawings of sulfonic acid group modified organic-inorganic hybrid mesoporous silica materials including (a) 3% SAM-PMO, (b) 6% SAM-PMO, (c) 12% SAM-PMO, and (d) 18% SAM-PMO.
Figure 26:
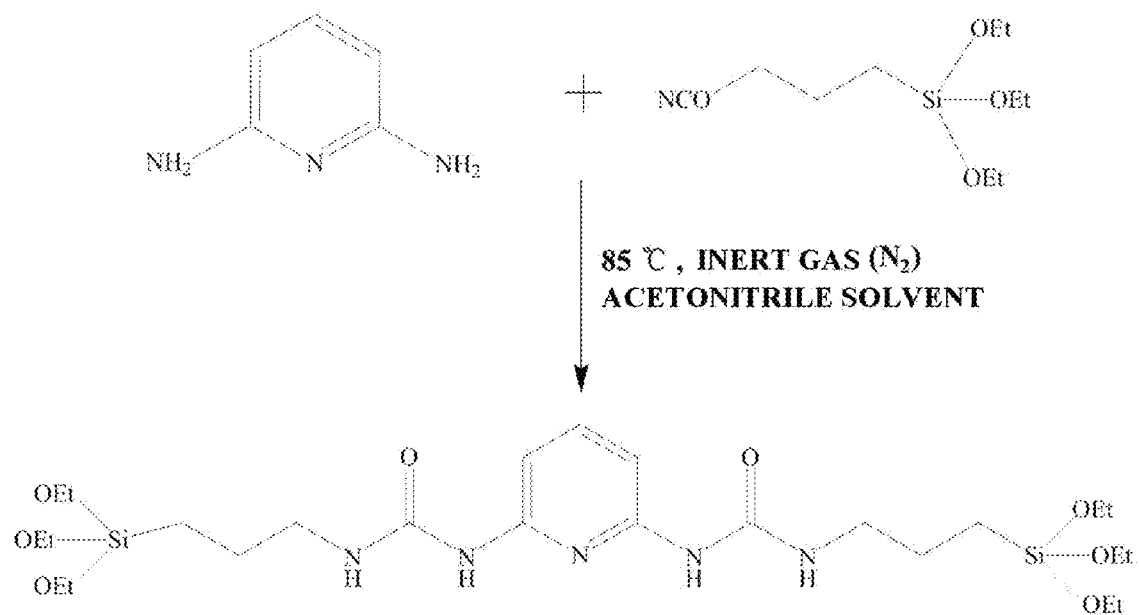
FIG. 26 illustrates a schematic diagram for explaining another synthetic process of an organic-inorganic hybrid precursor including a 2,6-diamino pyridine group, reported in a society of 'The 3$^{rd}$ Asian Symposium on Advanced materials (Sep. 19, 2011~Sep. 22, 2011)' by the present inventors.

FIG. 24 illustrates TEM (transmission electron microscopy) drawings of sulfonic acid group modified organic-inorganic hybrid mesoporous silica materials such as (a) 3% SAM-PMO, (b) 6% SAM-PMO, (c) 12% SAM-PMO, and (d) 18% SAM-PMO. In FIG. 24, (a) corresponds to 3% SAM-PMO, (b) corresponds to 6% SAM-PMO, (c) corresponds to 12% SAM-PMO, and (d) corresponds to 18% SAM-PMO.

When the amount of the 2,6-diamino pyridine precursor represented by DAP/TEOS=0.06 (6% SAM-PMO) or less, a porous structure of a regularly arranged hexahedral structure may be illustrated as (a) and (b) in FIG. 24. On the contrary, as the amount of the 2,6-diamino pyridine precursor increases to the ratio of DAP/TEOS=0.18 (18% SAM-PMO), a pore structure of a globular arrangement is shown and the regularity of the pore arrangement decreases as (c) and (d) in FIG. 24.

FIG. 25 is a table for illustrating an adsorbing amount and a selectivity of metal ions with respect to a solution including various metal ions dissolved therein and manufactured by using an aqueous solution (artificial seawater) having similar condition as the seawater, as a solvent.

An organic-inorganic hybrid mesoporous silica material modified by a sulfonic acid (SAM-PMO) and obtained by modifying an organic-inorganic hybrid mesoporous silica material obtained by mixing different amounts of an organic-inorganic hybrid precursor including a 2,6-diamino pyridine group, is used as an adsorbing agent.

When considering the adsorption result on the metal ions, 6% SAM-PMO among the organic-inorganic hybrid adsorption materials including the cross-linked sulfonic acid group in accordance with the present inventive concept, illustrates a very good selectivity of about 96% and an adsorption amount of about 4.49 mg/g with respect to cobalt ions among cobalt ions ($Co^{2+}$), chromium ions ($Cr^{3+}$), nickel ions ($Ni^{2+}$), copper ions ($Cu^{2+}$) and lithium ions ($Li^+$).

When the amount of the modified sulfonic acid group is increased to 12% SAM-PMO and 18% SAM-PMO, the selectivity is decreased to about 74% and about 52%, respectively. Though the amount of the sulfonic acid group included in the sample is increased, the surface area is remarkably decreased to about 64 m$^2$/g and about 18 m$^2$/g, respectively as illustrated in FIG. 22. This value is even lower value than the surface area of about 292 m$^2$/g with respect to a sample of 6% SAM-PMO. As illustrated in FIG. 18, the regularity of the pore arrangement is remarkably decreased. Due to the result, 6% SAM-PMO illustrates the highest selectivity with respect to the cobalt ions.

In accordance with the present inventive concept, an organic-inorganic hybrid mesoporous material has a high surface area (about 637 m$^2$/g), includes well arranged pores having a homogeneous pore size (about 43.0 Å) and a large pore volume (about 0.69 cm$^2$/g). The organic-inorganic hybrid mesoporous material may include a stable cross-linked functional group, which may be synthesized under an acidic condition and even under a strong acid condition.

In addition, an adsorbing agent having a high selectivity with respect to cobalt ions may be manufactured after modifying the organic-inorganic hybrid mesoporous material with a sulfonic acid group. Accordingly, economic budget on the whole national basis may be decreased when considering the rapid price increase of cobalt.

Further, the used adsorbing agent may be advantageously separated from a solution by means of a filtering method.

While the present invention has been described in detail, it should be understood that various changes, substitutions and alterations can be made hereto without departing from the spirit and scope of the invention as defined by the appended claims.

What is claimed is:

1. An organic-inorganic hybrid mesoporous silica material manufactured by using an organic-inorganic hybrid silica precursor and an alkoxy silica source as constituting materials of a porous wall, and a three-element copolymer as a template material for forming a structure, and by performing a self assembling method and a hydrothermal reaction,
    wherein said organic-inorganic hybrid silica precursor is prepared from 2,6-diamino pyridine, phosgene, and a silane compound including a functionalized amino group, the organic-inorganic hybrid silica precursor having the following chemical formula:

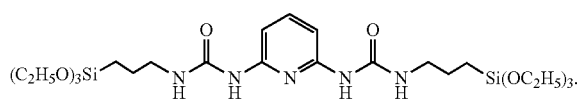

2. The organic-inorganic hybrid silica precursor of claim 1, wherein the silane compound is 3-aminopropyltriethoxysilane.

3. The organic-inorganic hybrid mesoporous silica material of claim 1, wherein a 2,6-diamino pyridine group cross-linked to an inner portion of the porous wall is modified by using a sulfonic acid group.

4. The organic-inorganic hybrid mesoporous silica material of claim 3, wherein the modification is performed by using chlorosulfonic acid and triethyl amine (Et3N).

5. An organic-inorganic hybrid mesoporous adsorbing agent, having a selective adsorptivity on specific metal ions, the adsorbing agent being obtained by modifying a surface of pores of the organic-inorganic hybrid mesoporous silica material of claim 1 by a sulfonic acid group through adding chlorosulfonic acid to the organic-inorganic hybrid mesoporous silica material and then treating using triethylamine (Et3N).

6. The organic-inorganic hybrid mesoporous adsorbing agent of claim 5, wherein the specific metal ion includes a cobalt ion (Co2+).

7. The organic-inorganic hybrid mesoporous adsorbing agent of claim 6, wherein the selective adsorptivity on the cobalt ion (Co2+) is about 96% or over.

8. The organic-inorganic hybrid mesoporous adsorbing agent of claim 5, wherein a mixing ratio of the silica precursor based on the alkoxy silicon source is about 6%.

9. A method of manufacturing an organic-inorganic hybrid mesoporous adsorbing agent, the method comprising:
    forming a silica precursor including a cross-linked 2,6-diamino pyridine group by using 2,6-diamino pyridine, phosgene and 3-aminopropyltriethoxysilane;
    forming a silica/template hybrid including a cross-linked 2,6-diamino pyridine group by mixing a template for forming a structure of an organic material, with a silica precursor and tetraethyl orthosilicate (TEOS);
    removing the template from the silica/template hybrid and forming an organic-inorganic hybrid mesoporous silica material; and
    modifying the surface of pores of the organic-inorganic hybrid mesoporous silica material by using a sulfonic acid group.

10. The method of claim 9, wherein a mixing ratio of the silica precursor based on tetraethyl orthosilicate is about 6%.

* * * * *